United States Patent
Lee et al.

(10) Patent No.: US 9,212,178 B2
(45) Date of Patent: Dec. 15, 2015

(54) SUBSTITUTED PYRIMIDINE COMPOUNDS AND THEIR USE AS SYK INHIBITORS

(71) Applicants: Genosco, Santa Fe Springs, CA (US); Oscotec, Inc., Seongnam, Gyeonggi-Do (KR)

(72) Inventors: Jaekyoo Lee, North Andover, MA (US); Jang-Sik Choi, Cheonan-Si (KR); Hae-Jun Hwang, Yongin (KR); Ho-Juhn Song, Andover, MA (US); Jung-Ho Kim, Seongnam (KR); Se-Won Kim, Seongnam (KR); Jong Sung Koh, Gyeonggi-do (KR); Jaesang Lee, Belmont, MA (US); Tae-Im Lee, Gwangju (KR); Yung-Geun Choi, Suwon (KR); Sung-Ho Park, Gwangmyeong (KR); In Yong Lee, Belmont, MA (US); Byung-Chul Suh, Lexington, MA (US); Paresh Devidas Salgaonkar, Medford, MA (US); Dong-Sik Jung, Cheonan (KR)

(73) Assignees: Genosco, Santa Fe Springs, CA (US); Oscotec, Inc., Seongnam (KR)

( * ) Notice: Subject to any disclaimer, the term of this patent is extended or adjusted under 35 U.S.C. 154(b) by 0 days.

(21) Appl. No.: 14/520,279

(22) Filed: Oct. 21, 2014

(65) Prior Publication Data

US 2015/0111883 A1    Apr. 23, 2015

Related U.S. Application Data

(60) Provisional application No. 61/893,866, filed on Oct. 21, 2013.

(51) Int. Cl.
*A61K 31/506* (2006.01)
*C07D 413/14* (2006.01)
*A61K 31/5355* (2006.01)

(52) U.S. Cl.
CPC ............ *C07D 413/14* (2013.01); *A61K 31/506* (2013.01); *A61K 31/5355* (2013.01)

(58) Field of Classification Search
CPC . C07D 413/14; A61K 31/506; A61K 31/5355
See application file for complete search history.

(56) References Cited

U.S. PATENT DOCUMENTS 8,637,529 B2 * 1/2014 Woller et al. .............. 514/262.1
8,871,778 B2 * 10/2014 Choi ................. A61K 31/5377 514/275
8,877,763 B2 * 11/2014 Kim ..................... C07D 471/04 514/264.11

FOREIGN PATENT DOCUMENTS

| WO | WO-2007042299 A1 | 4/2007 | |
|---|---|---|---|
| WO | WO-2009032694 A1 | 3/2009 | |
| WO | WO-2011060295 A1 | 5/2011 | |
| WO | WO 2011060295 A1 * | 5/2011 | ........... A61K 31/505 |
| WO | WO-2013109882 A1 | 7/2013 | |

OTHER PUBLICATIONS

R. Singh et al., 42 Annual Reports in Medicinal Chemistry, 379-391, 380 (2007).*
M. Riccaboni et al., 15 Drug Discovery Today, 517-530 (2010).*
M.E. Weinblatt et al., 363 The New England Journal of Medicine 1303-1312 (2010).*
N. Yamamoto et al., 306 The Journal of Pharmacology and Experimental Therapeutics, 1174-1181 (2003).*
E.S. Masuda et al., 21 Pulmonary Pharmacology & Therapeutics, 461-467 (2008).*
M. Gonzalez et al., 22 Expert Opinion Therapeutic Patents, 1289-1302 (2012).*
S. Malhotra et al., 11 Expert Opinion Therapeutic Patents, 275-291 (2006).*
International Search Report and Written Opinion for Application No. PCT/US2014/061649, 13 pages, dated Feb. 17, 2015.

* cited by examiner

*Primary Examiner* — Alexander R Pagano
(74) *Attorney, Agent, or Firm* — Mintz Levin Cohn Ferris Glovsky and Popeo, P.C.; Kongsik Kim

(57) ABSTRACT

Compounds of Formula (I) and methods for inhibiting kinases, including spleen tyrosine kinases, are disclosed. Also disclosed are methods for treating a kinase-mediated disease or condition by administering to a subject a therapeutically effective amount of the compound of Formula (I).

Formula I

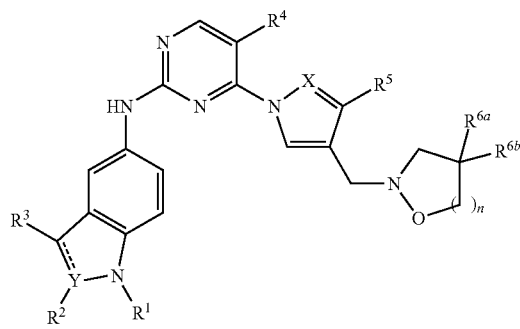

19 Claims, No Drawings

SUBSTITUTED PYRIMIDINE COMPOUNDS AND THEIR USE AS SYK INHIBITORS

RELATED APPLICATIONS

This application claims the benefit of and priority to U.S. Provisional Application No. 61/893,866, filed Oct. 21, 2013, the contents of which are incorporated herein by reference.

BACKGROUND OF THE INVENTION

SYK (Spleen Tyrosine Kinase) is an intracellular tyrosine kinase that is involved in coupling activated immunoreceptors to signal downstream events that mediate diverse cellular responses, including proliferation, differentiation and phagocytosis.

The receptors in which SYK performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1 R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Ruzza et al., Expert Opin. Ther. Patents, 2009, 19 (10), 1361-1376; Ulanova et al., Expert Opin. Ther., Target., 2005, 9 (5), 901-921; Wang et al., J. Immunol., 2006, 177, 6859-6870; Slack et el., European J. Immunol., 2007, 37, 1600-1612).

Dysregulation and/or misregulation of different signal transduction pathways of SYK in different cell types have been implicated in numerous diseases and disorders e.g., allergic rhinitis, asthma, autoimmune diseases, rheumatoid arthritis (RA), osteopenia, osteoporosis, COPD and various leukemia and lymphomas. The inhibition of SYK activity by the present invention may offer a therapeutic option for treatment of many diseases associated with SYK activity.

Rheumatoid arthritis (RA) is an auto-immune disease characterized by inflammation of articular joints leading to debilitating destruction of bone and cartilage.

Studies using cells from SYK knocked-out mice displayed characteristic phenotypes by blocking in B cell development (M. Turner et al., Nature, 1995, 378, 298-302; Cheng et al., Nature, 1995, 378, 303-306). These studies and elsewhere demonstrate that SYK is required for the differentiation and activation of B cells. Therefore, inhibition of SYK activity in RA patients is likely to block B cell function and hence to reduce rheumatoid factor production. In addition to the role of SYK in B cell function, the requirement for SYK activity in Fc receptor (FcR) signaling is relevant to treatment of RA. FcR activation by immune complexes in RA has been suggested to contribute to the release of multiple pro-inflammatory mediators.

It was demonstrated that targeting B cell function by antibody rituximab, a B cell depleting antibody is an appropriate therapeutic strategy to treat auto-immune diseases such as RA (Edwards et al., New Eng. J. Med., 2004, 350 (25), 2572-2581). Furthermore, genetic deficiency of SYK in the hematopoietic compartment completely blocked the development of all macroscopic and microscopic signs of arthritis in autoantibody-induced arthritis mice model. In addition, it was demonstrated that the SYK$^{-/-}$ mutation prevented the appearance of periarticular bone erosions. Finally, SYK$^{-/-}$ bone marrow chimeras were completely protected from arthritis-induced loss of articular function (Jakus et al., Arthritis Rheum., 2010, 62 (7), 1899-1910).

SYK inhibitors may also be useful in treatment of systemic lupus erythematosus (SLE) which is a chronic inflammatory autoimmune disease and can affect several organs and systems. Several studies have shown that T-cell receptor (TCR) signaling is modified in patients suffering from SLE (Tsokos G C., N Engl J Med, 2011, 365, 2110-2121). Instead of transmitting signals through TCR to CD3ζ and Zap70, an alternative pathway comes into play involving FcRγ and SYK ([Krishnan et l., J Immunol., 2008, 181, 8145-8152). FcRγ is homologous in shape and function to CD3 and takes its place in SLE T cells and associates with Syk. This alternative FcRγ/Syk duet is 100 times enzymatically more potent than the canonical CD3ζ/Zap70. As a result, following activation, SLE T cells exhibit higher intracytoplasmic calcium flux and cytosolic protein tyrosine phosphorylation (Nambiar et al., J. Immunol., 2003, 170, 2871-2876).

SYK inhibitors may also be useful in cancer therapy, specifically heme malignancies, particularly Non-Hodgkin's Lymphomas including follicular (FL), mantle cell, Burkitt and diffuse large B cell (DLBCL) lymphomas. SYK is found to be dysregulated by overexpression and/or constitutively activation in a variety of primary B-lymphoma tumors and in B-lymphoma cell lines. Through the PI3K/AKT pathway, the PLD pathway and AKT independent signalling, SYK is known to activate mTOR (mammalian target of rapamycin) which in turn increases B-cell survival and proliferation Inhibition of SYK in vitro results in decreased mTOR activation and a reduction of clonicity in FL cells and diffuse large B cell lymphoma (DLBCL) (Lesux L. et al., Blood, 2006, 108(13), 4156-4162 and Guruajan M. et al., J. Immun., 2007, 178, 111-121).

SYK inhibitors may also be useful in the treatment of asthma and rhinitis. Allergic rhinitis and asthma are diseases associated with hypersensitivity reactions and inflammatory events involving a multitude of cell types including mast cells, eosinophils, T cells and dendritic cells. SYK is positioned in transducing the downstream cellular signals associated with cross-linking FcεR1 and FcγR1 receptors. Following exposure to allergen, high affinity immunoglobulin receptors for IgE (FcεR1) and IgG (FcγR1) become cross-linked and activate downstream processes in mast cells and other cell types leading to release of pro-inflammatory mediators and airway spasmogens. In the mast cell, for example, IgE receptor cross-linking by allergen leads to release of mediators including histamine from preformed granules, as well as the synthesis and release of newly synthesized lipid mediators including prostaglandins and leukotrienes, which lead inflammatory events.

SYK inhibitors may also be useful in the treatment of urticaria triggered by allergic reactions but many cases have an unclear etiology. Acute and chronic urticaria are common skin diseases. There are many pathological similarities in chronic urticaria patients with allergen-induced mast and basophil cell degranulation reactions via IgE activation. Around 40% of chronic spontaneous urticaria patients contain serum IgG auto-antibodies targeting IgE or the FcεR and these are thought to drive the histamine and other mediator release via mast and basophil degranulation. SYK inhibitors would inhibit the signaling response post IgE medicated FcεR activation and inhibit the mediator release known to be involved in chronic pruritis in multiple diseases.

An inhibitor of the SYK kinase activity could also be used therapeutically in treating chronic obstructive pulmonary disease (COPD) caused by microbes and allegens. COPD is characterised by a successive deterioration in lung function and chronic inflammation of the airways, which is initiated and produced by noxious substances of all kinds and contributes to the maintenance of the course of the disease. At a cellular level, in COPD there is in particular a multiplication of T lymphocytes, neutrophils, granulocytes and macrophages. An increase in the number of CD8-positive lymphocytes is known to be directly connected with the impairment of lung function. Another characteristic of COPD are acute deteriorations in lung function (exacerbations), characterised by viral (e.g. Rhinovirus), or bacterial (e.g. *Streptococcus pneumoniae*, *Haemophilus influenzae* and *Moraxella catarrhalis*) infections. An inhibitor of the SYK kinase activity could also be used therapeutically in acute lung deteriorations caused by Rhinoviruses.

WO03/057695A1 (Boehringer Ingelheim Pharmaceuticals, Inc.) describes novel 1,6-naphthyridines that have SYK inhibitory activity. Three more recent patent applications, WO2010/015518A2, WO2010/015520A1 and WO2011/092128A1 (Boehringer Ingelheim International GmbH) disclose compounds having SYK inhibitory activity.

WO04/035604A2 (Millennium Pharmaceuticals, Inc.) discloses the structural co-ordinates of the human SYK protein.

WO 2011/134971 A1 (Glaxo Group Ltd.) discloses 7-(1H-pyrazol-4-yl)-1,6-naphthyridine compounds as SYK inhibitors.

WO 2011/144585 A1 (F. Hoffmann-La Roche A G) discloses the pyrrolo[2,3-B]pyrazine-7-carboxamide derivatives and their use as JAK and SYK inhibitors.

There remains, however, a need to identify further compounds which are inhibitors of spleen tyrosine kinase (SYK).

SUMMARY OF THE INVENTION

The present invention relates to novel chemical compounds that display inhibition activity against the protein kinase SYK (Spleen Tyrosine Kinase), the preparation and formulation thereof and their use for therapy.

The present invention provides pyrimidine derivatives represented by Formula (I) and their use for the treatment of conditions such as respiratory complaints, allergic diseases, osteopenia, osteoporosis, gastrointestinal diseases, autoimmune diseases, inflammatory diseases and diseases of the peripheral or central nervous system, asthma, allergic rhinitis, rheumatoid arthritis, allergic dermatitis and COPD, and various leukemia and lymphomas, or other conditions treatable by inhibiting SYK activity.

The present invention provides a compound of Formula (I), as well as pharmacologically acceptable salts, diastereomers, enantiomers, racemates, hydrates or solvates thereof,

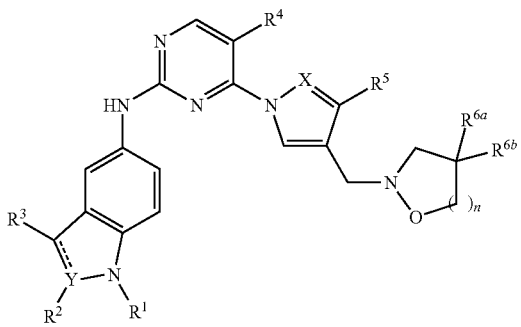

Formula (I)

Wherein:
$R^1$, $R^2$, $R^3$, $R^4$, $R^5$, $R^{6a}$, $R^{6b}$, X and Y are as described herein:
X is CH or N;
Y is C, CH or N;
n is 1 or 2;

==== is a single or a double bond, provided that if Y is C, then ==== represents a double bond;

When Y is N or CH and ==== represents a double bond, $R^2$ is absent;

$R^1$ is selected from H, $C_1$-$C_6$alkyl, $C_3$-$C_7$cycloalkyl, $C_5$-$C_8$heterocycloalkyl, aryl, arylalkyl, heteroaryl, C(O)OR$^7$, and S(O)$_2$R$^7$, wherein $C_1$-$C_6$ alkyl, $C_5$-$C_8$heterocycloalkyl, aryl, arylalkyl, or heteroaryl is optionally substituted with one or more halo, hydroxy, or OR$^7$;

When Y is C and ==== represents a double bond, or when Y is CH or N and ==== represents a single bond, then, $R^2$ is selected from H, halo, $CF_3$, $C_1$-$C_4$alkyl and aryl, wherein the $C_1$-$C_4$alkyl or aryl is optionally substituted with one or more halo, amino, hydroxy, alkoxy, or haloalkyl;

$R^3$ is selected from H, halo, C(O)NR$^7$R$^7$, C(O)R$^7$, S(O)$_m$R$^7$, and S(O)$_m$NR$^7$R$^7$, wherein each m is 1 or 2;

$R^4$ is selected from H, halo, $C_1$-$C_6$alkyl, and $C_3$-$C_7$cycloalkyl, wherein the $C_1$-$C_6$alkyl, or $C_3$-$C_7$cycloalkyl is optionally substituted with one or more halo, amino, hydroxy, alkoxy, or haloalkyl;

$R^5$ is selected from H, halo, $C_1$-$C_6$alkyl, and $C_3$-$C_7$cycloalkyl, wherein $C_1$-$C_6$alkyl or $C_3$-$C_7$cycloalkyl is optionally and independently substituted with one or more halo, alkoxy, or haloalkyl;

$R^{6a}$ is selected from H, halo, hydroxy, CN, $CH_2OH$, $NH_2$, $C_1$-$C_6$alkyl, $C_3$-$C_7$cycloalkyl, $C_6$-$C_{10}$aryl, heteroaryl, OR$^7$, NR$^7$R$^7$, NHR$^7$, and NHC(O)R$^7$;

$R^{6b}$ is selected from H, $CH_2OH$, $CH_2NH_2$, and $C_1$-$C_6$alkyl;

$R^7$ is independently selected from $C_1$-$C_6$ alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, and heterocycloalkyl, wherein the $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocycloalkyl is optionally and independently substituted with one or more substituents selected from aryl, cycloalkyl, heteroaryl, heterocycloalkyl, alkyl, halo, amino, and hydroxy;

or a pharmaceutically acceptable salt thereof.

In one aspect, the present invention provides pharmaceutical compositions comprising a compound of Formula (I) and a pharmaceutically acceptable carrier. In certain embodiments, such pharmaceutical compositions are formulated for intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration. In other embodiments, such pharmaceutical composition are formulated as tablets, pills, capsules, a liquid, an inhalant, a nasal spray solution, a suppository, a solution, a gel, an emulsion, an ointment, eye drops or ear drops.

In one aspect, the present invention provides methods for treating a cell-proliferative disease or condition, such as cancer, comprising administering to a subject in need of such treatment a therapeutically effective amount of the compound of Formula (I) or pharmaceutically acceptable salts, pharmaceutical compositions or medicaments thereof, wherein the cell proliferative disease or condition include, for example, B-cell and/or T cell-lymphoma. In one aspect, the present invention provides methods of inhibiting growth of cancer cells with a compound of Formula (I) or a pharmaceutically acceptable salt thereof.

In another aspect, the present invention provides a medicament for treating a SYK-mediated disease, disorder or condition in a patient comprising a therapeutically effective amount of the compound of Formula (I).

In another aspect, the present invention provides methods for inhibiting protein kinases, comprising administering to a subject in need thereof, a therapeutically effective amount of the compound of Formula (I) or a pharmaceutically acceptable salt or pharmaceutical composition thereof. The protein kinase includes, but is not limited to, SYK kinase.

In another aspect, the present invention provides methods for inhibiting protein kinases, comprising contacting a cell with a compound of Formula (I). In certain embodiment, the compound of Formula (I) effectively inhibits activity of one or more kinases and associated mutants selected from SYK, MLK1, or PLK3. In certain embodiments, protein kinase-mediated diseases or conditions are inflammatory diseases or conditions, respiratory diseases or autoimmune diseases or conditions, such as asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, rheumatoid arthritis, multiple sclerosis, cancer, breast cancer, HIV associated diseases or systemic lupus erythematosus (SLE).

In another aspect, the present invention provides methods of treating a kinase-mediated disease or condition by administering to a subject a therapeutically effective amount of the compound of Formula (I) or a pharmaceutically acceptable salt, in combination with a second therapeutic agent.

In another aspect, the invention relates to the use of the compounds of the invention for the preparation of a medicament for the treatment of a kinase-mediated disease or condition.

The present invention also relates to compositions comprising these compounds, methods of making these compounds, methods of inhibiting enzyme activity, particularly SYK kinase activity, through use of these compounds, and method of treating disease or disease symptoms in a mammal, particularly where inhibition of the kinase activity, can affect disease outcome.

Other aspects and embodiments of the invention will be apparent from the following description.

DETAILED DESCRIPTION OF THE INVENTION

The present invention provides a group of substituted pyrimidine derivatives and pharmaceutically acceptable salts thereof that are useful for inhibiting SYK kinase activity and for treating diseases and disorders that are mediated by SYK kinase such as inflammatory diseases including rheumatoid arthritis, autoimmune diseases including systemic lupus erythematosus (SLE) and rhinitis, cancer including leukemia, lymphoma, and osteoporosis. The present invention also provides methods of preparing pyrimidine derivatives. The present invention also provides pharmaceutical formulations comprising at least one of the compounds of the present invention together with a pharmaceutically acceptable carrier, diluent or excipient thereof. The invention also provides useful intermediates generated during syntheses of the pyrimidine derivative compounds.

The present invention provides a compound of Formula (I), or individual stereoisomer, mixture of isomers, or pharmaceutically acceptable salt thereof,

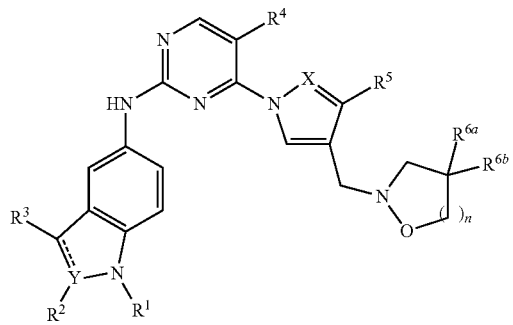

Formula (I)

wherein:
$R^1$, $R^2$, $R^3$, $R^4$, $R^5$, $R^{6a}$, $R^{6b}$, X and Y are as described herein:
X is CH or N;
Y is C, CH or N;
n is 1 or 2;
==== is a single or a double bond, provided that if Y is C, then ==== represents a double bond;
When Y is N or CH and ==== represents a double bond, $R^2$ is absent;
$R^1$ is selected from H, $C_1$-$C_6$alkyl, $C_3$-$C_7$cycloalkyl, $C_5$-$C_8$heterocycloalkyl, aryl, arylalkyl, heteroaryl, C(O)OR$^7$, and S(O)$_2$R$^7$, wherein $C_1$-$C_6$ alkyl, $C_5$-$C_8$heterocycloalkyl, aryl, arylalkyl, or heteroaryl is optionally substituted with one or more halo, hydroxy, or OR$^7$;
When Y is C and ==== represents a double bond, or when Y is CH or N and ==== represents a single bond, then,
$R^2$ is selected from H, halo, CF$_3$, $C_1$-$C_4$alkyl and aryl, wherein the $C_1$-$C_4$alkyl or aryl is optionally substituted with one or more halo, amino, hydroxy, alkoxy, or haloalkyl;
$R^3$ is selected from H, halo, C(O)NR$^7$R$^7$, C(O)R$^7$, S(O)$_m$R$^7$, and S(O)$_m$NR$^7$R$^7$, wherein each m is 1 or 2;
$R^4$ is selected from H, halo, $C_1$-$C_6$alkyl, and $C_3$-$C_7$cycloalkyl, wherein the $C_1$-$C_6$alkyl, or $C_3$-$C_7$cycloalkyl is optionally substituted with one or more halo, amino, hydroxy, alkoxy, or haloalkyl;
$R^5$ is selected from H, halo, $C_1$-$C_6$alkyl, and $C_3$-$C_7$cycloalkyl, wherein $C_1$-$C_6$alkyl or $C_3$-$C_7$cycloalkyl is optionally and independently substituted with one or more halo, alkoxy, or haloalkyl;
$R^{6a}$ is selected from H, halo, hydroxy, CN, CH$_2$OH, NH$_2$, $C_1$-$C_6$alkyl, $C_3$-$C_7$cycloalkyl, $C_6$-$C_{10}$aryl, heteroaryl, OR$^7$, NR$^7$R$^7$, NHR$^7$, and NHC(O)R$^7$;
$R^{6b}$ is selected from H, CH$_2$OH, CH$_2$NH$_2$, and $C_1$-$C_6$alkyl;
$R^7$ is independently selected from $C_1$-$C_6$ alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, and heterocycloalkyl, wherein the $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocycloalkyl is optionally and independently substituted with one or more substituents selected from aryl, cycloalkyl, heteroaryl, heterocycloalkyl, alkyl, halo, amino, and hydroxy;
or a pharmaceutically acceptable salt thereof.

In certain embodiments, $R^1$ is selected from H, methyl, ethyl, propyl, isopropyl, butyl, cyclopropyl, cyclobutyl, cyclopentyl, 2-hydroxyethyl, 2-methoxyethyl, 2,2,2-trifluoroethyl, 2-fluoroethyl, ethylcarboxyl, methylsulfonyl, or cyclopropylmethyl.

In certain embodiments, Y is C or CH.

In certain embodiments, $R^2$ is H, halo, $CF_3$, $C_1$-$C_4$alkyl or aryl, wherein the $C_1$-$C_4$alkyl or aryl is optionally substituted with one or more halo, alkoxy, or haloalkyl.

In certain embodiments, Y is N.

In certain embodiments, $R^3$ is H, halo, $C(O)NR^7R^7$, $C(O)R^7$, $S(O)_mR^7$, $S(O)_mNR^7R^7$, wherein each m is 1 or 2.

In certain embodiments, $R^3$ is selected from acetyl, propionyl, cyclopropyl carbonyl, fluoromethyl carbonyl, difluoromethyl carbonyl, trifluoromethyl carbonyl, methanesulfonyl, ethanesulfonyl, cyclopropanesulfonyl, benzenesulfonyl, p-toluenesulfonyl, N,N-dimethylaminocarbonyl, morpholinylcarbonyl, or pyrrolidinylcarbonyl.

In certain embodiments, $R^4$ is selected from H, F, Cl, Br, $CH_3$, $CF_3$, ethyl, cyclopropyl, or cyclobutyl.

In certain embodiments, $R^5$ is selected from H, Cl, Br, $CH_3$, $CF_3$, ethyl, isopropyl, cyclopropyl, cyclobutyl, or phenyl.

In certain embodiments, $R^{6a}$ is selected from halo, hydroxy, CN, $CH_2OH$, $NH_2$, $C_1$-$C_6$alkyl, $C_3$-$C_7$cycloalkyl, $C_6$-$C_{10}$aryl, heteroaryl, $OR^7$, $NR^7R^7$, $NHR^7$, and $NHC(O)R^7$.

In certain embodiments, $R^{6a}$ is hydroxy (—OH).

In certain embodiments, $R^{6b}$ is H. In certain embodiments, $R^{6a}$ is hydroxyl and $R^{6b}$ is H.

In another aspect, the invention provides a compound selected from the group consisting of:
(S)-cyclopropyl(5-(4-(4-((4-hydroxyisoxazolidin-2-yl)methyl)-3-methyl-1H-pyrazol-1-yl)pyrimidin-2-ylamino)-1-methyl-1H-indol-3-yl)methanone;
(S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)-2-methylpropan-1-one;
(S)-2,2,2-trifluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;
(S)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;
(S)-ethyl 3-acetyl-5-(4-(4-((4-hydroxyisoxazolidin-2-yl)methyl)-3-methyl-1H-pyrazol-1-yl)pyrimidin-2-ylamino)-1H-indole-1-carboxylate;
(S)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone;
(S)-2,2,2-trifluoro-1-(5-(4-(4-((4-hydroxyisoxazolidin-2-yl)methyl)-3-methyl-1H-pyrazol-1-yl)pyrimidin-2-ylamino)-1H-indol-3-yl)ethanone;
(S)-cyclopropyl(5-(4-(4-((4-hydroxyisoxazolidin-2-yl)methyl)-3-methyl-1H-pyrazol-1-yl)pyrimidin-2-ylamino)-1-isopropyl-1H-indol-3-yl)methanone;
(S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;
(R)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;
(R)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone;
(S)-cyclopropyl(5-(4-(4-((4-hydroxyisoxazolidin-2-yl)methyl)-3-methyl-1H-pyrazol-1-yl)pyrimidin-2-ylamino)-1H-indol-3-yl)methanone;
cyclopropyl(1-ethyl-5-(4-(4-((4-hydroxy-4-methylisoxazolidin-2-yl)methyl)-3-methyl-1H-pyrazol-1-yl)pyrimidin-2-ylamino)-1H-indol-3-yl)methanone;
cyclopropyl(5-(4-(4-((4-hydroxy-4-methylisoxazolidin-2-yl)methyl)-3-methyl-1H-pyrazol-1-yl)pyrimidin-2-ylamino)-1-methyl-1H-indol-3-yl)methanone;
(S)-cyclopropyl(5-(4-(4-((4-hydroxyisoxazolidin-2-yl)methyl)-3-methyl-1H-pyrazol-1-yl)pyrimidin-2-ylamino)-1-(2,2,2-trifluoroethyl)-1H-indol-3-yl)methanone;
cyclopropyl(5-(4-(4-((4-hydroxy-4-methylisoxazolidin-2-yl)methyl)-3-methyl-1H-pyrazol-1-yl)pyrimidin-2-ylamino)-1-(2,2,2-trifluoroethyl)-1H-indol-3-yl)methanone;
(S)-1-(5-(5-chloro-4-(4-((4-hydroxyisoxazolidin-2-yl)methyl)-3-methyl-1H-pyrazol-1-yl)pyrimidin-2-ylamino)-1-methyl-1H-indol-3-yl)-2,2,2-trifluoroethanone;
(S)-2,2,2-trifluoro-1-(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)ethanone;
(S)-cyclopropyl(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)methanone;
(S)-cyclopropyl(1-ethyl-5-(5-fluoro-4-(4-((4-hydroxyisoxazolidin-2-yl)methyl)-3-methyl-1H-pyrazol-1-yl)pyrimidin-2-ylamino)-1H-indol-3-yl)methanone;
(S)-cyclopropyl(1-ethyl-5-(5-fluoro-4-(3-((4-hydroxyisoxazolidin-2-yl)methyl)-4-methyl-1H-pyrrol-1-yl)pyrimidin-2-ylamino)-1H-indol-3-yl)methanone;
(S)-cyclopropyl(1-ethyl-5-(4-(4-((4-hydroxyisoxazolidin-2-yl)methyl)-3-methyl-1H-pyrazol-1-yl)-5-methylpyrimidin-2-ylamino)-1H-indol-3-yl)methanone;
(S)-cyclopropyl(1-(2-fluoroethyl)-5-(4-(4-((4-hydroxyisoxazolidin-2-yl)methyl)-3-methyl-1H-pyrazol-1-yl)pyrimidin-2-ylamino)-1H-indol-3-yl)methanone;
cyclopropyl(1-(2-fluoroethyl)-5-(4-(4-(((S)-4-hydroxyisoxazolidin-2-yl)methyl)-3-methyl-1H-pyrazol-1-yl)pyrimidin-2-ylamino)indolin-3-yl)methanone;
(S)-cyclopropyl(5-(4-(3-cyclopropyl-4-((4-hydroxyisoxazolidin-2-yl)methyl)-1H-pyrazol-1-yl)pyrimidin-2-ylamino)-1-ethyl-1H-indol-3-yl)methanone;
(S)-2-((3-methyl-1-(2-(1-methyl-3-(methylsulfonyl)-1H-indazol-5-ylamino)pyrimidin-4-yl)-1H-pyrazol-4-yl)methyl)isoxazolidin-4-ol;
(S)-cyclopropyl(5-(4-(4-((4-hydroxyisoxazolidin-2-yl)methyl)-3-methyl-1H-pyrazol-1-yl)pyrimidin-2-ylamino)-1-(methylsulfonyl)-1H-indol-3-yl)methanone;
(S)-cyclopropyl(1-ethyl-5-(4-(3-((4-hydroxyisoxazolidin-2-yl)methyl)-4-methyl-1H-pyrrol-1-yl)pyrimidin-2-ylamino)-1H-indol-3-yl)methanone;
(S)-cyclopropyl(5-(4-(4-((4-hydroxyisoxazolidin-2-yl)methyl)-1H-pyrazol-1-yl)pyrimidin-2-ylamino)-1-methyl-1H-indol-3-yl)methanone;
(S)-2-((1-(2-(3-chloro-1,2-dimethyl-1H-indol-5-ylamino)pyrimidin-4-yl)-3-methyl-1H-pyrazol-4-yl)methyl)isoxazolidin-4-ol;
(S)-cyclopropyl(1-(2-fluoroethyl)-5-(4-(4-((4-hydroxyisoxazolidin-2-yl)methyl)-1H-pyrazol-1-yl)pyrimidin-2-ylamino)-1H-indol-3-yl)methanone;
(S)-cyclopropyl(1-(2,2-difluoroethyl)-5-(4-(4-((4-hydroxyisoxazolidin-2-yl)methyl)-1H-pyrazol-1-yl)pyrimidin-2-ylamino)-1H-indol-3-yl)methanone; and
(S)-cyclopropyl(5-(4-(4-((4-hydroxyisoxazolidin-2-yl)methyl)-1H-pyrazol-1-yl)pyrimidin-2-ylamino)-1-(2,2,2-trifluoroethyl)-1H-indol-3-yl)methanone; or a pharmaceutically acceptable salt thereof.

In another aspect, the invention provides a pharmaceutical formulation comprising a compound of the invention (i.e., a compound of Formula (I)), in combination with a pharmaceutically acceptable carrier, diluent, or excipient.

In another aspect, the invention provides the use of compound of Formula (I)) for the treatment of a disease or condition as described herein. In certain embodiments, the invention provides a compound or pharmaceutically acceptable salt thereof of Formula (I), for use in the treatment of an autoimmune condition, the inflammatory diseases and/or allergic disorders such as systemic lupus erythematosus (SLE), discoid (cutaneous) lupus, Sjorgens syndrome, Wegners graulomatosis and other vasculitides, idiopathic thrombocytopenic purpura, giant cell arteriosis, glomerulonephritis, chronic transplant rejection, chronic obstructive pulmonary disease, adult respiratory distress syndrome, asthma, severe asthma, ulcerative colitis, Crohn's disease, bronchitis, conjunctivitis, psoriasis, scleroderma, (contact and allergic) dermatitis, allergy, (allergic) rhinitis, allergic rhinoconjunctivitis, autoimmune bullous conditions including pemphigus and pemphigoid, mastocytosis, anaphylaxis, chronic (spontaneous) urticaria, Berger's disease, Evans's syndrome, granulocytopenia, Goodpasture's syndrome, hepatitis, Henoch-Schonlein purpura, multiple sclerosis, immunohaemolytic anaemia, autoimmune haemolytic anemia, Kawasaki syndrome. In certain embodiments, the invention provides Formula (I) compound or pharmaceutically acceptable salt thereof of Formula (I), for use in the treatment of rheumatoid arthritis and osteoporosis, osteolytic diseases and osteopenia. In certain embodiments, the invention provides a compound or pharmaceutically acceptable salt thereof of Formula (I), for use in the treatment of heme malignancies, particularly Non-Hodgkin's Lymphomas including follicular (FL), mantle cell, capsule cell lymphoma, neutropenia, small lymphocytic lymphoma, chronic lymphocytic lymphoma, Burkitt and diffuse large B cell lymphomas and T-cell lymphoma.

In another aspect, the invention provides a method for treating a condition selected from an autoimmune condition, an inflammatory disease, or an allergic disorder, the method comprising administering to a patient in need of such treatment an effective amount of a compound of Formula (I). In certain embodiments, the condition is systemic lupus erythematosus (SLE), discoid (cutaneous) lupus, Sjorgens syndrome, Wegners graulomatosis and other vasculitides, idiopathic thrombocytopenic purpura, giant cell arteriosis, glomerulonephritis, chronic transplant rejection, chronic obstructive pulmonary disease, adult respiratory distress syndrome, asthma, severe asthma, ulcerative colitis, Crohn's disease, bronchitis, conjunctivitis, psoriasis, scleroderma, (contact and allergic) dermatitis, allergy, (allergic) rhinitis, allergic rhinoconjunctivitis, pemphigus, pemphigoid, mastocytosis, anaphylaxis, chronic (spontaneous) urticaria, Berger's disease, Evans's syndrome, granulocytopenia, Goodpasture's syndrome, hepatitis, Henoch-Schonlein purpura, multiple sclerosis, immunohaemolytic anaemia, autoimmune haemolytic anemia, or Kawasaki syndrome. In certain embodiments, the compound is administered singly or in combination with one or more additional therapeutic agents. In certain embodiments, the compound is administered via intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration.

In another aspect, the invention provides a method for treating a heme malignancy, the method comprising administering to a patient in need thereof an effective amount of a compound or pharmaceutically acceptable salt thereof of Formula (I). In certain embodiments, the heme malignancy is selected from the group consisting of Non-Hodgkin's Lymphomas including follicular (FL), mantle cell, capsule cell lymphoma, neutropenia, small lymphocytic lymphoma, chronic lymphocytic lymphoma, Burkitt and diffuse large B cell lymphomas and T-cell lymphoma.

In another aspect, the invention provides a process for preparing a compound of Formula (I), the process comprising:

i. reacting a compound of formula (a) with a compound of formula (b) in a first organic solvent in the presence of a first base to give a compound of formula (c);

ii. reacting the compound of formula (c) with an aniline derivative of formula (d) in the presence of a second base, a ligand and a palladium catalyst in a second solvent to give a compound of formula (e);

iii. reacting the compound of formula (e) with an amine derivative (f) in a third organic solvent in the presence of reducing agent such as $NaBH(OAc)_3$ to give a compound of Formula (I); or iv. reacting the compound of formula (c) with an amine derivative (f) in a fourth organic solvent in the presence of reducing agent such as $NaBH(OAc)_3$ to give a compound of formula (g);

v. reacting the compound of formula (g) with an aniline derivative formula (d) in the presence of a second base and a palladium catalyst to give a compound of Formula (I);

or the compound of formula (e) is prepared by the following steps:

vi. reacting a compound of formula (h) with a compound of formula (i) in the presence of a first base in a second organic solvent to give a compound of formula (j);

vii. reacting the compound of formula (j) with a compound of formula (b) in a second organic solvent in the presence of a first base to give a compound of formula (e);

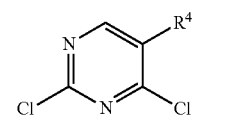

a

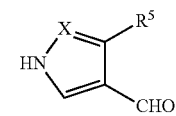

b

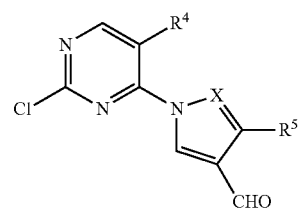

c

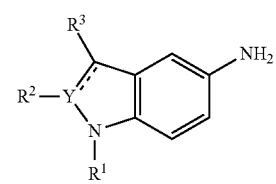

d

-continued

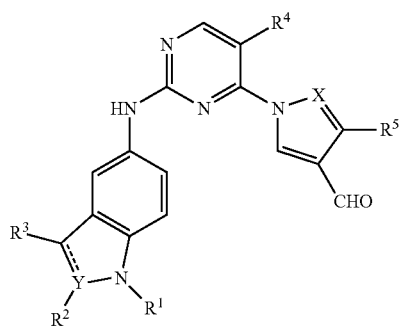

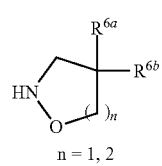
n = 1, 2

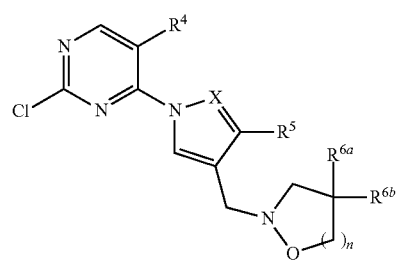

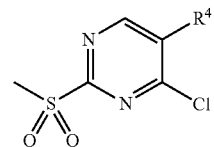

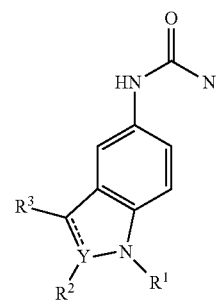

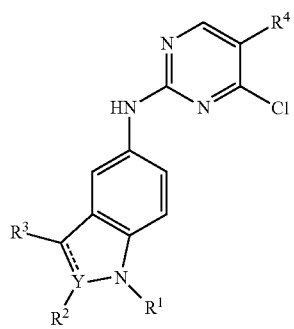

-continued e

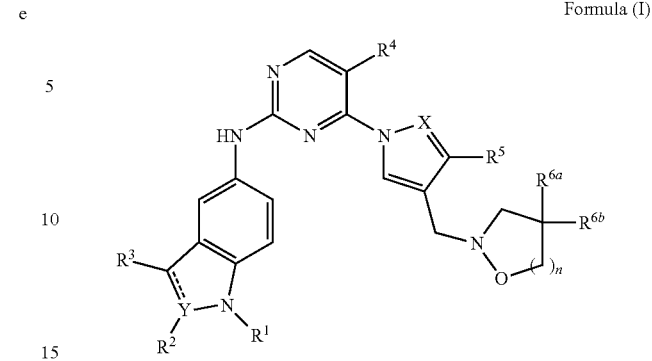

Formula (I)

f wherein: $R^1$, $R^2$, $R^3$, $R^4$, $R^5$, $R^{6a}$, $R^{6b}$, n, X and Y are as described for Formula (I).

In certain aspects, the invention also provides (i) a method of preparing a compound of formula (c) by reacting a compound of formula (a) with a compound of formula (b) in the presence of the first base in the first organic solvent (see Scheme 1); (ii) a method of preparing a compound of formula (e) by reacting the compound of formula (c) with aniline derivatives (d) in the presence of the second base, ligand, and a palladium catalyst in the second organic solvent (see Scheme 1); (iii) a method of preparing a compound of Formula (I) by reductive amination of the compound of formula (e) and an amine derivative by using a reducing agent in the third solvent (see Scheme 1). The invention also provides a method of preparing a compound of Formula (I) according to Scheme 1 (Method 1).

Scheme 1 (Method 1)

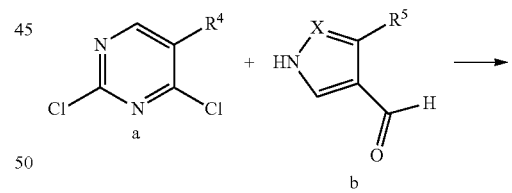

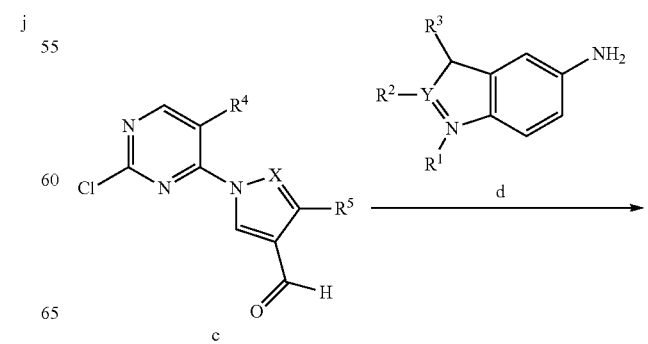

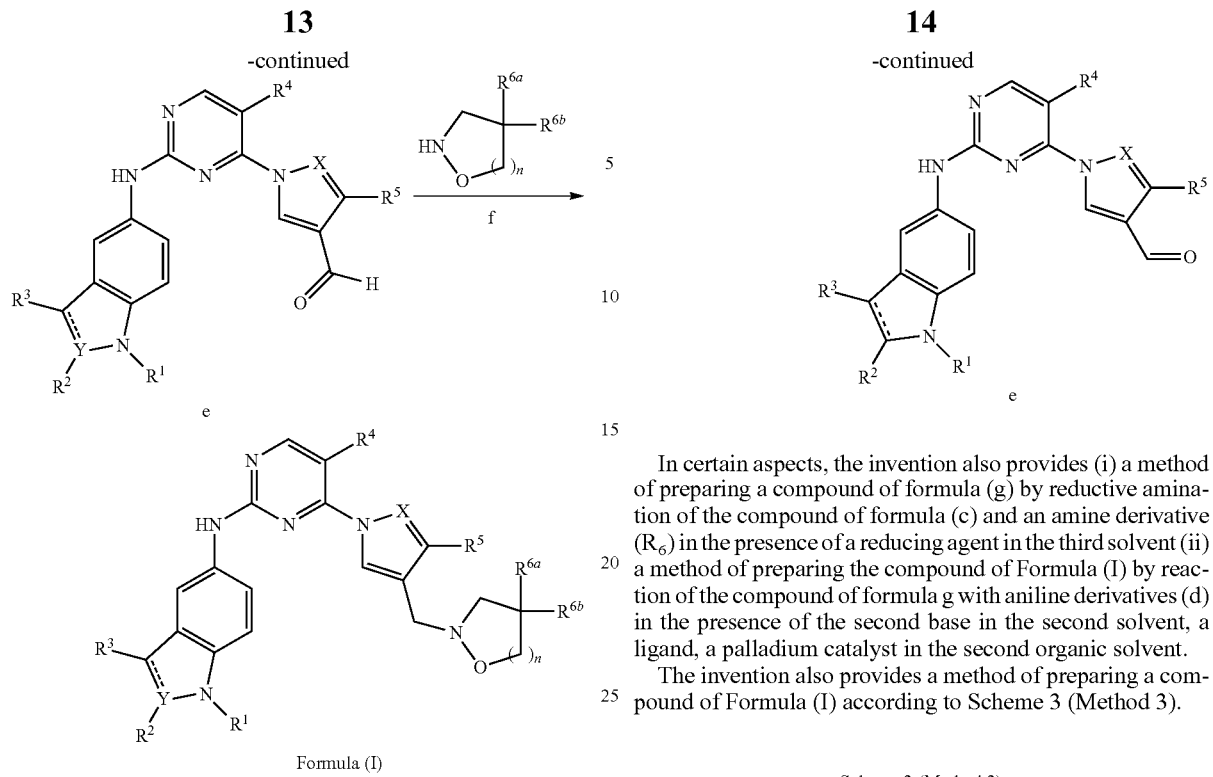

In certain aspects, the invention also provides (i) a method of preparing a compound of formula (j) from the compound of formula (i) and 4-chloro-2-(methylsulfonyl)pyrimidine (h) by reaction with NaH in the first solvent; (ii) a method of preparing a compound of formula (e) from the compound of formula (j) and formula (b) in the presence of NaH in the first solvent (Method 2).

In certain aspects, the invention also provides (i) a method of preparing a compound of formula (g) by reductive amination of the compound of formula (c) and an amine derivative $(R_6)$ in the presence of a reducing agent in the third solvent (ii) a method of preparing the compound of Formula (I) by reaction of the compound of formula g with aniline derivatives (d) in the presence of the second base in the second solvent, a ligand, a palladium catalyst in the second organic solvent.

The invention also provides a method of preparing a compound of Formula (I) according to Scheme 3 (Method 3).

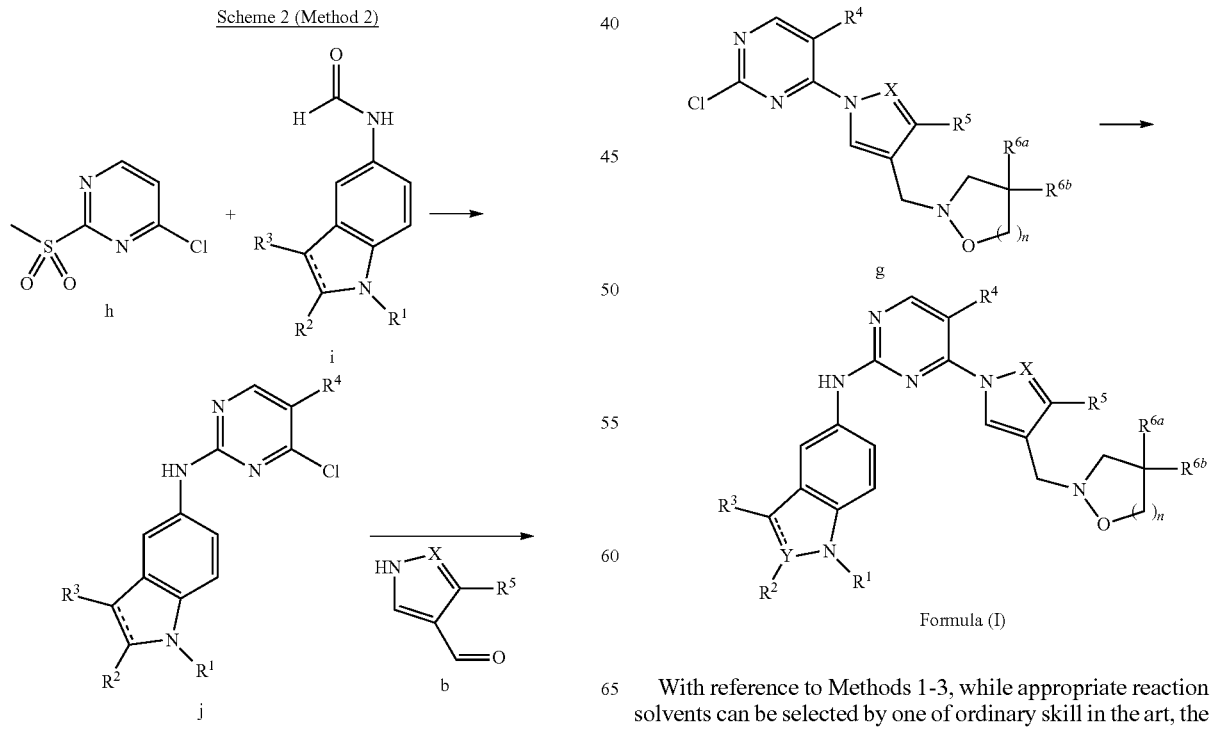

With reference to Methods 1-3, while appropriate reaction solvents can be selected by one of ordinary skill in the art, the first organic solvent is generally selected from relatively polar, aprotic solvents such as acetone, tetrahydrofuran, N,N-dimethylformamide, dichloromethane, dichloroethane, or acetonitrile; the second organic solvent is generally selected from aprotic solvents such as toluene, dioxane, tetrahydrofuran, N,N-dimethylformamide, N,N-dimethylacetamide or N-methylmorpholine; the third organic solvent is generally selected from relatively polar, solvents such as tetrahydrofuran, methanol, ethanol, dichloromethane, dichloroethane, N,N-dimethylacetamide or N,N-dimethylformamide; the fourth solvent is generally selected from relatively polar, protic solvents such as methanol, ethanol, tert-butanol or water, and fifth solvent is generally selected from solvents such as dichloromethane, ethyl acetate, acetone, or water.

With reference to Methods 1-3, while bases and other reactants can be selected by one of ordinary skill in the art, the first base is generally selected from bases such as $K_2CO_3$, $Cs_2CO_3$, NaOH, KOH, NaH, tert-BuOK, ter-BuONa, triethylamine, or diisopropylethylamine; the second base is generally selected from bases such as tert-BuOK, tert-BuONa, $Cs_2CO_3$, or $K_2CO_3$; the third base is selected generally from bases such as NaH, n-BuLi, $Cs_2CO_3$; a palladium catalyst is generally selected from $Pd(OAc)_2$, $Pd_2(dba)_3$, or $Pd(dppf)Cl_2$; a ligand is generally selected from BiNap, Xantphose, or S-Phose; the oxidizing agent is selected from oxidizing agents such as m-chloroperbenzoic acid (mCPBA) or oxone; and the reducing agent is generally selected from $NaBH(OAc)_3$, $NaBH_4$, or $NaBH(CN)_3$.

In certain embodiments, the invention provides a method for preparing a compound of Formula (I), the method comprising reacting a compound of formula (g)

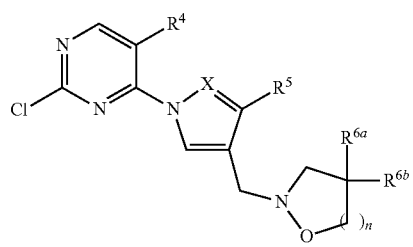

in which $R^4$, $R^5$, $R^{6a}$, $R^{6b}$, n and X are as defined in Formula (I), with an aniline derivative of formula (d)

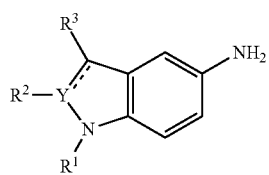

in which Y, $R^1$, $R^2$, and $R^3$ are as defined in Formula (I), in the presence of a base and a palladium catalyst under conditions such that a compound of Formula I is prepared.

Representative compounds of Formula (I) are listed below in Table 1.

TABLE 1

Representative compounds of Formula (I)

TABLE 1-continued

Representative compounds of Formula (I)

| No | Structure |
|---|---|
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |

TABLE 1-continued
Representative compounds of Formula (I)
| No | Structure |
|----|-----------|
| 15 | 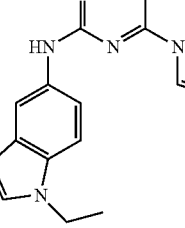 |
| 17 | 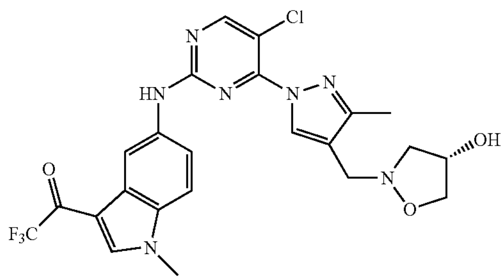 [SMILES: Cc1nn(-c2nc(Nc3ccc4c(c3)c(C(=O)C(F)(F)F)cn4C)ncc2Cl)cc1CN1C[C@H](O)CO1] |
| 18 | 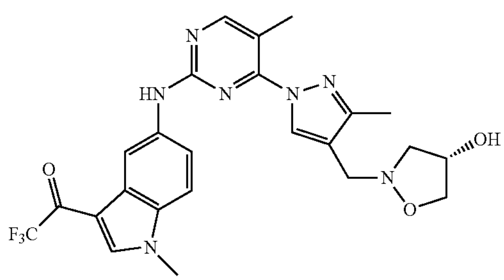 [SMILES: Cc1cnc(Nc2ccc3c(c2)c(C(=O)C(F)(F)F)cn3C)nc1-n1cc(CN2C[C@H](O)CO2)c(C)n1] |
| 19 | 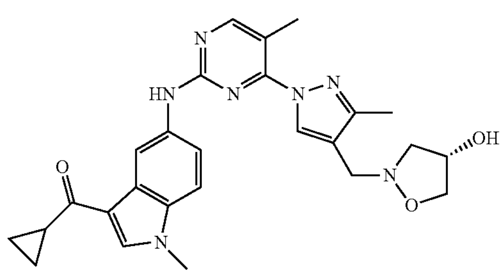 [SMILES: Cc1cnc(Nc2ccc3c(c2)c(C(=O)C2CC2)cn3C)nc1-n1cc(CN2C[C@H](O)CO2)c(C)n1] |
| 21 | 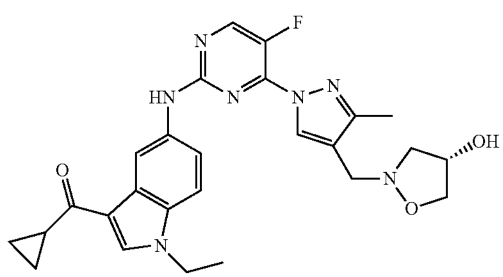 [SMILES: CCn1cc(C(=O)C2CC2)c2cc(Nc3ncc(F)c(-n4cc(CN5C[C@H](O)CO5)c(C)n4)n3)ccc21] |
TABLE 1-continued
Representative compounds of Formula (I)
| No | Structure |
|----|-----------|
| 21 | 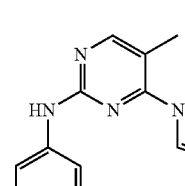 |
| 22 | 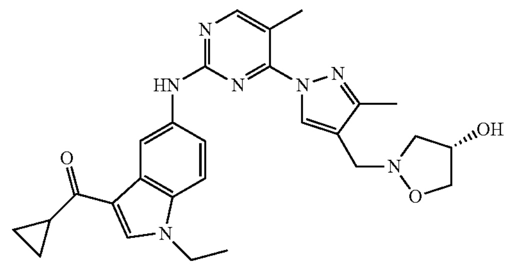 |
| 23 | 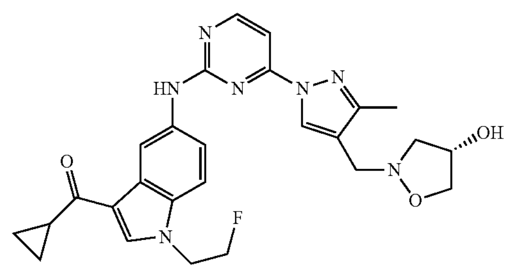 [SMILES: Cc1nn(-c2ccnc(Nc3ccc4c(c3)c(C(=O)C3CC3)cn4CCF)n2)cc1CN1C[C@H](O)CO1] |
| 24 | 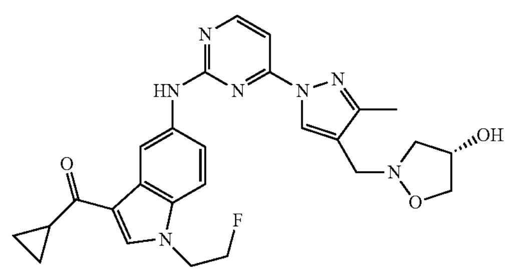 |
| 25 | 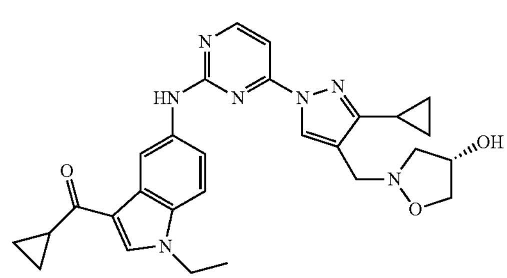 [SMILES: CCn1cc(C(=O)C2CC2)c2cc(Nc3nccc(-n4cc(CN5C[C@H](O)CO5)c(C5CC5)n4)n3)ccc21] |

TABLE 1-continued

Representative compounds of Formula (I)

| No | Structure |
|---|---|
| 26 | (structure) |
| 27 | (structure) |
| 28 | (structure) |
| 29 | (structure) |
| 30 | (structure) |
| 31 | (structure) |
| 32 | (structure) |
| 33 | (structure) |
| 34 | (structure) |

The compounds in Table 1 are named as follows:

(S)-cyclopropyl(5-(4-(4-((4-hydroxyisoxazolidin-2-yl)methyl)-3-methyl-1H-pyrazol-1-yl)pyrimidin-2-ylamino)-1-methyl-1H-indol-3-yl)methanone;

(S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)-2-methylpropan-1-one;

(S)-2,2,2-trifluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;

(S)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;

(S)-ethyl 3-acetyl-5-(4-(4-((4-hydroxyisoxazolidin-2-yl)methyl)-3-methyl-1H-pyrazol-1-yl)pyrimidin-2-ylamino)-1H-indole-1-carboxylate;

(S)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone;

(S)-2,2,2-trifluoro-1-(5-(4-(4-((4-hydroxyisoxazolidin-2-yl)methyl)-3-methyl-1H-pyrazol-1-yl)pyrimidin-2-ylamino)-1H-indol-3-yl)ethanone;

(S)-cyclopropyl(5-(4-(4-((4-hydroxyisoxazolidin-2-yl)methyl)-3-methyl-1H-pyrazol-1-yl)pyrimidin-2-ylamino)-1-isopropyl-1H-indol-3-yl)methanone;

(S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;

(R)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;

(R)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone;

(S)-cyclopropyl(5-(4-(4-((4-hydroxyisoxazolidin-2-yl)methyl)-3-methyl-1H-pyrazol-1-yl)pyrimidin-2-ylamino)-1H-indol-3-yl)methanone;

cyclopropyl(1-ethyl-5-(4-(4-((4-hydroxy-4-methylisoxazolidin-2-yl)methyl)-3-methyl-1H-pyrazol-1-yl)pyrimidin-2-ylamino)-1H-indol-3-yl)methanone;

cyclopropyl(5-(4-(4-((4-hydroxy-4-methylisoxazolidin-2-yl)methyl)-3-methyl-1H-pyrazol-1-yl)pyrimidin-2-ylamino)-1-methyl-1H-indol-3-yl)methanone;

(S)-cyclopropyl(5-(4-(4-((4-hydroxyisoxazolidin-2-yl)methyl)-3-methyl-1H-pyrazol-1-yl)pyrimidin-2-ylamino)-1-(2,2,2-trifluoroethyl)-1H-indol-3-yl)methanone;

cyclopropyl(5-(4-(4-((4-hydroxy-4-methylisoxazolidin-2-yl)methyl)-3-methyl-1H-pyrazol-1-yl)pyrimidin-2-ylamino)-1-(2,2,2-trifluoroethyl)-1H-indol-3-yl)methanone;

(S)-1-(5-(5-chloro-4-(4-((4-hydroxyisoxazolidin-2-yl)methyl)-3-methyl-1H-pyrazol-1-yl)pyrimidin-2-ylamino)-1-methyl-1H-indol-3-yl)-2,2,2-trifluoroethanone;

(S)-2,2,2-trifluoro-1-(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)ethanone;

(S)-cyclopropyl(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)methanone;

(S)-cyclopropyl(1-ethyl-5-(5-fluoro-4-(4-((4-hydroxyisoxazolidin-2-yl)methyl)-3-methyl-1H-pyrazol-1-yl)pyrimidin-2-ylamino)-1H-indol-3-yl)methanone;

(S)-cyclopropyl(1-ethyl-5-(5-fluoro-4-(3-((4-hydroxyisoxazolidin-2-yl)methyl)-4-methyl-1H-pyrrol-1-yl)pyrimidin-2-ylamino)-1H-indol-3-yl)methanone;

(S)-cyclopropyl(1-ethyl-5-(4-(4-((4-hydroxyisoxazolidin-2-yl)methyl)-3-methyl-1H-pyrazol-1-yl)-5-methylpyrimidin-2-ylamino)-1H-indol-3-yl)methanone;

(S)-cyclopropyl(1-(2-fluoroethyl)-5-(4-(4-((4-hydroxyisoxazolidin-2-yl)methyl)-3-methyl-1H-pyrazol-1-yl)pyrimidin-2-ylamino)-1H-indol-3-yl)methanone;

cyclopropyl(1-(2-fluoroethyl)-5-(4-(4-(((S)-4-hydroxyisoxazolidin-2-yl)methyl)-3-methyl-1H-pyrazol-1-yl)pyrimidin-2-ylamino)indolin-3-yl)methanone;

(S)-cyclopropyl(5-(4-(3-cyclopropyl-4-((4-hydroxyisoxazolidin-2-yl)methyl)-1H-pyrazol-1-yl)pyrimidin-2-ylamino)-1-ethyl-1H-indol-3-yl)methanone;

(S)-2-((3-methyl-1-(2-(1-methyl-3-(methylsulfonyl)-1H-indazol-5-ylamino)pyrimidin-4-yl)-1H-pyrazol-4-yl)methyl)isoxazolidin-4-ol;

(S)-cyclopropyl(5-(4-(4-((4-hydroxyisoxazolidin-2-yl)methyl)-3-methyl-1H-pyrazol-1-yl)pyrimidin-2-ylamino)-1-(methylsulfonyl)-1H-indol-3-yl)methanone;

cyclopropyl(5-(4-(4-((4-hydroxy-4-methylmorpholino)methyl)-1H-pyrazol-1-yl)pyrimidin-2-ylamino)-1-methyl-1H-indol-3-yl)methanone;

(S)-cyclopropyl(1-ethyl-5-(4-(3-((4-hydroxyisoxazolidin-2-yl)methyl)-4-methyl-1H-pyrrol-1-yl)pyrimidin-2-ylamino)-1H-indol-3-yl)methanone;

(S)-cyclopropyl(5-(4-(4-((4-hydroxyisoxazolidin-2-yl)methyl)-1H-pyrazol-1-yl)pyrimidin-2-ylamino)-1-methyl-1H-indol-3-yl)methanone;

(S)-2-((1-(2-(3-chloro-1,2-dimethyl-1H-indol-5-ylamino)pyrimidin-4-yl)-3-methyl-1H-pyrazol-4-yl)methyl)isoxazolidin-4-ol;

(S)-cyclopropyl(1-(2-fluoroethyl)-5-(4-(4-((4-hydroxyisoxazolidin-2-yl)methyl)-1H-pyrazol-1-yl)pyrimidin-2-ylamino)-1H-indol-3-yl)methanone;

(S)-cyclopropyl(1-(2,2-difluoroethyl)-5-(4-(4-((4-hydroxyisoxazolidin-2-yl)methyl)-1H-pyrazol-1-yl)pyrimidin-2-ylamino)-1H-indol-3-yl)methanone;

(S)-cyclopropyl(5-(4-(4-((4-hydroxyisoxazolidin-2-yl)methyl)-1H-pyrazol-1-yl)pyrimidin-2-ylamino)-1-(2,2,2-trifluoroethyl)-1H-indol-3-yl)methanone; or a pharmaceutically acceptable salt thereof.

The term "alkyl," used alone or as part of a larger moiety such as "arylalkyl" or "cycloalkyl" refers to a straight or branched hydrocarbon radical having from 1 to 15 carbon atoms, or from 1-8 carbon atoms, or from 1-6 carbon atoms, or from 1-4 carbon atoms (unless stated otherwise) and includes, for example, methyl, ethyl, n-propyl, iso-propyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group having from 3 to 10 carbon atoms, or from 3 to 7 carbon atoms, in the hydrocarbon ring (unless stated otherwise) and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, and oxygen.

The term "heterocycloalkyl" means a non-aromatic monocyclic or polycyclic ring having from 2 to 9 carbon atoms, or from 2 to 7 carbon atoms, in the ring (unless stated otherwise) and at least one heteroatom, preferably, 1 to 4 heteroatoms selected from nitrogen, sulfur (including oxidized sulfur such as sulfone or sulfoxide) and oxygen. The ring or ring system of the heterocycloalkyl group can be linked to another moiety of the compound via a carbon atom or a nitrogen atom, if such an atom is present. A heterocycloalkyl group can have a total of 3-10, or 3-8, or 5-8, atoms in the ring system (unless otherwise stated). A heterocycloalkyl group can have one or more carbon-carbon double bonds or carbon-heteroatom double bonds in the ring group as long as the ring group is not rendered aromatic by their presence.

Examples of heterocycloalkyl groups include azetidinyl, aziridinyl, pyrrolidinyl, piperidinyl, piperazinyl, homopiperazinyl, morpholino, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halo" includes fluoro, chloro, bromo, and iodo.

As used herein, the term "alkoxy" refers to the alkyl groups above bound through oxygen, examples of which include methoxy, ethoxy, iso-propoxy, tert-butoxy, and the like. In addition, alkoxy also refers to polyethers such as —O—(CH$_2$)$_2$—O—CH$_3$, and the like. An alkoxy can be unsubstituted or substituted with one or more suitable substituents.

As used herein, the term "aryl" refers to unsubstituted or substituted aromatic monocyclic or polycyclic groups and includes, for example, carbocyclic aromatic groups such as phenyl, naphthyl and the like, as well as heteroaromatic groups such as pyridyl, furanyl, thiophenyl, and the like. The term "aryl" also includes an aromatic ring (such as a phenyl or pyridyl ring) fused to a non-aromatic carbocyclic or heterocyclic ring. The term "aryl" may be interchangeably used with "aryl ring," aromatic group," and "aromatic ring." Heteroaryl groups have 4 to 14 atoms in the heteroaromatic ring(s), 1 to 9 of which are independently selected from the group consisting of oxygen, sulfur and nitrogen. Heteroaryl groups have 1-3 heteroatoms in a 5-8 membered aromatic group. An aryl or heteroaryl can be a mono- or bicyclic aromatic group. Typical aryl and heteroaryl groups include, for example, phenyl, quinolinyl, indazoyl, indolyl, dihydrobenzodioxynyl, 3-chlorophenyl, 2,6-dibromophenyl, pyridyl, pyrimidinyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like. An aryl or heteroaryl can be unsubstituted or substituted with one or more suitable substituents.

As used herein, the term "haloalkyl" refers to any alkyl radical having one or more hydrogen atoms replaced by a halogen atom. Examples of haloalkyl include —CF3, —CFH$_2$, —CF$_2$H, and the like.

As used herein, the term "hydroxyl" or "hydroxy" refers to —OH.

As used herein, the term "amino" refers to —NH$_2$.

As used herein, the term "hydroxyalkyl" refers to any hydroxyl derivative of alkyl radical. The term "hydroxyalkyl" includes any alkyl radical having one or more hydrogen atoms replaced by a hydroxy group.

As used herein, the term "arylalkyl" includes any alkyl radical having one or more hydrogen atoms replaced by an aryl group, e.g., a benzyl group, a phenethyl group, and the like.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents by other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halo, alkyl, haloalkyl, aryl, hydroxy, alkoxy, hydroxyalkyl, amino, and the like.

As used herein, the term "inhibitor" refers to a compound which inhibits one or more kinases described herein. For example, the term "SYK inhibitor" refers to a compound which inhibits the SYK receptor or reduces the signaling effect.

As used herein, the term "pharmaceutically acceptable" refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein.

As used herein, the term "pharmaceutical combination" means a product that results from the mixing or combining of more than one active ingredient.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "prodrug" refers to an agent that is converted into the parent drug in vivo.

As used herein, the term "protein kinase-mediated disease" or a "disorder or disease or condition mediated by inappropriate protein kinase activity" refers to any disease state mediated or modulated by protein kinases described herein. Such disease states include, but are not limited to, systemic lupus erythematosus (SLE), asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, bullous disorders, collagenoses, contact dermatitis eczema, Kawasaki Disease, rosacea, Sjogren-Larsso Syndrome, rheumatoid arthritis, multiple sclerosis, inflammatory bowel syndrome, HIV, diffuse large B cell lymphoma, Non-Hodgkin lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, gastrointestinal cancer, Alzheimer's disease, Parkinson's disease, osteoporosis, osteopenia, osteomalacia, osteofibrosis, Paget's disease, diabetes, blood vessel proliferative disorders, ocular diseases, cardiovascular disease, restenosis, fibrosis, atherosclerosis, arrhythmia, angina, myocardial ischemia, myocardial infarction, cardiac or vascular aneurysm, vasculitis, stroke, peripheral obstructive arteriopathy, reperfusion injury following ischemia of an organ or a tissue, endotoxic, surgical or traumatic shock, hypertension, valvular heart disease, heart failure, abnormal blood pressure, vasoconstriction, vascular abnormality, transplant rejection and infectious diseases including viral and fungal infections.

As used herein, the term "kinase-mediated disease" or "kinase-mediated disease" or a "disorder or disease or condition mediated by inappropriate kinase activity" refers to any disease state mediated or modulated by a kinase mechanism. For example "SYK-mediated disease" refers to any disease state mediated or modulated by SYK mechanisms. Such SYK-mediated disease states include, but are not limited to, inflammatory, respiratory diseases and autoimmune diseases, such as, by way of example only, rheumatoid arthritis, systemic lupus erythematosus (SLE), asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, rheumatoid arthritis, multiple sclerosis, cancer, HIV-associated disease and non-Hodgkin lymphoma including diffuse large B cell lymphoma.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "solvate" refers to a complex of variable stoichiometry formed by a solute (in this invention, a compound of Formula (I) or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "administration" or "administering" of the subject compound refers to providing a compound of the invention and/or prodrugs thereof to a subject in need of treatment.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "effective amount" or "therapeutically effective amount" refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. By way of example only, a therapeutically effective amount of a compound of the invention may be in the range of e.g., about 0.01 mg/kg/day to about 100 mg/kg/day, or from about 0.1 mg/kg/day to about 10 mg/kg/day.

1. Human Protein Kinases

The compounds of the present invention were screened against the kinase panel and inhibited the activity of at least one kinase on the panel. Examples of kinases include, but are not limited to SYK and mutant forms thereof.

The compounds described herein are inhibitors of SYK kinase activity and have therapeutic benefit in the treatment of disorders associated with inappropriate kinase activity, in particular in the treatment and prevention of disease states mediated by kinases, including SYK kinase. Therefore, the present invention provides methods of regulating and, in particular, inhibiting signal transduction cascades in which a kinase plays a role. The method generally involves administering to a subject or contacting a cell expressing the kinase with an effective amount of a compound described herein, prodrug, or an acceptable salt, hydrate, solvate, N-oxide and/or composition thereof, to regulate or inhibit the signal transduction cascade. The methods are also used to regulate and, in particular, inhibit downstream processes or cellular responses elicited by activation of the particular kinase signal transduction cascade. The methods are also practiced in in vitro contexts or in in vivo contexts as a therapeutic approach towards the treatment or prevention of diseases characterized by, caused by, or associated with activation of the kinase-dependent signal transduction cascade.

2. Pharmaceutical Compositions

For the therapeutic uses of compounds provided herein, including compounds of Formula (I), or pharmaceutically acceptable salts, solvates, N-oxides, prodrugs, or isomers thereof, such compounds are administered in therapeutically effective amounts either alone or as part of a pharmaceutical composition. Accordingly, provided herein are pharmaceutical compositions, which comprise at least one compound provided herein, including at least one compound of Formula (I), pharmaceutically acceptable salts and/or solvates thereof, and one or more pharmaceutically acceptable carriers, diluents, adjuvant or excipients. In addition, such compounds and compositions are administered singly or in combination with one or more additional therapeutic agents. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or optic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The therapeutically effective amount will vary depending on, among others, the disease indicated, the severity of the disease, the age and relative health of the subject, the potency of the compound administered, the mode of administration and the treatment desired. The required dosage will also vary depending on the mode of administration, the particular condition to be treated and the effect desired.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of the invention may be prepared from the corresponding base addition salt or acid addition salt form, respectively. For example a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug derivatives of the compounds of the invention may be prepared by methods known to those of ordinary skill in the art (e.g., for further details see Saulnier et al., Bioorg. Med. Chem. Letters, 1994, 4, 1985; the entire teachings of which are incorporated herein by reference).

Protected derivatives of the compounds of the invention may be prepared by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference.

Compounds of the invention may be prepared as their individual stereoisomers by reaction of a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet and Samuel H. Wilen, "Enantiomers, Racemates and Resolutions," John Wiley And Sons, Inc., 1981, the entire teachings of which are incorporated herein by reference.

Suitable pharmaceutically acceptable carriers, diluents, adjuvants, or excipients for use in the pharmaceutical compositions of the invention include tablets (coated tablets) made of for example collidone or shellac, gum Arabic, talc, titanium dioxide or sugar, capsules (gelatin), solutions (aqueous or aqueous-ethanolic solution), syrups containing the active substances, emulsions or inhalable powders (of various saccharides such as lactose or glucose, salts and mixture of these excipients with one another) and aerosols (propellant-containing or -free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

Exemplary methods for preparing the compounds of the invention are described herein, including in the Examples.

In certain embodiments, compounds of Formula (I) are made by:
(a) optionally converting a compound of the invention into a pharmaceutically acceptable salt; (b) optionally converting a salt form of a compound of the invention to a non-salt form; (c) optionally converting an unoxidized form of a compound of the invention into a pharmaceutically acceptable N-oxide; (d) optionally resolving an individual isomer of a compound of the invention from a mixture of isomers; (e) optionally converting a non-derivatized compound of the invention into a pharmaceutically acceptable prodrug derivative; and (f) optionally converting a prodrug derivative of a compound of the invention to its non-derivatized form.

The teachings of all patents, published applications and references cited herein are incorporated by reference in their entirety.

EXAMPLES

The present invention is further exemplified by the following examples that illustrate the preparation of compounds of Formula (I) according to the invention. The examples are for illustrative purpose only and are not intended, nor should they be construed as limiting the invention in any manner. Those skilled in the art will appreciate that variations and modifications can be made without changing the scope of the invention.

Nuclear magnetic resonance (NMR) and mass spectrometry (MS) spectra obtained for compounds described in the examples below and those described herein were consistent with that of the compounds of formulae herein.

Liquid chromatography-mass spectrometry (LC-MS) Method:
1. Samples are run on Agilent Technologies 6120 MSD system with a Zorbax Eclipse XDB-C18 (3.5µ) reverse phase column (4.6×50 mm) run at room temperature with flow rate of 1.5 mL/minute.

2. The mobile phase uses solvent A (water/0.1% formic acid) and solvent B (acetonitrile/0.1% formic acid): 95%/5% to 0%/100% (A/B) for 5 minute.

3. The mass spectra (m/z) were recorded using electrospray ionization (ESI).

4. Ionization data was rounded to the nearest integer.

Proton NMR Spectra:

Unless otherwise indicated, all ¹H NMR spectra are run on a Varian series Mercury 300 MHz. All observed protons are reported as parts-per-million (ppm) downfield from tetramethylsilane using conventional abbreviations for designation of major peaks: e.g., s (singlet), d (doublet), t (triplet), q (quartet), m (multiplet) and brs (broad singlet).

Preparation of 1-(2-chloropyrimidin-4-yl)-3-methyl-1H-pyrazole-4-carbaldehyde; Intermediate 1

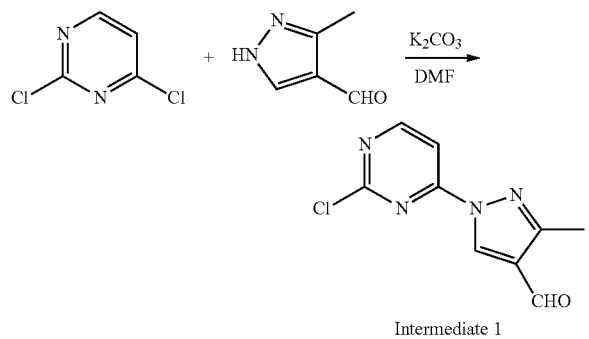

To a solution of ethyl 3-methyl-1H-pyrazole-4-carbaldehyde (6.4 g, 58.0 mmol) in 60 mL of anhydrous N,N-dimethylformamide were added potassium carbonate (10.8 g, 77.8 mmol) and 2,4-dichloropyrimidine (8.64 g, 58.0 mmol) at room temperature. The resulting suspension was stirred for 14 hours at room temperature with monitoring a reaction with LC-MS or thin layer chromatography (TLC). The reaction mixture was diluted with ethyl acetate and washed with brine (×2). The collected organic layer was dried over anhydrous sodium sulfate and then concentrated in vacuo. The resulting residue was purified by silica gel chromatography using a mixture of heptanes and ethyl acetate to afford the desired intermediate 1 as a white solid (5.47 g, 42%); MS (ESI) m/z 223 [M+H]⁺, ¹H NMR (300 MHz, CDCl₃) δ 10.06 (s, 1H), 9.04 (s, 1H), 8.70 (d, 1H, J=5.4 Hz), 7.87 (1H, d, J=5.4 Hz), 2.59 (s, 3H).

Method 1; (S)-cyclopropyl(5-(4-(4-((4-hydroxyisoxazolidin-2-yl)methyl)-3-methyl-1H-pyrazol-1-yl)pyrimidin-2-ylamino)-1-methyl-1H-indol-3-yl)methanone; Compound 1

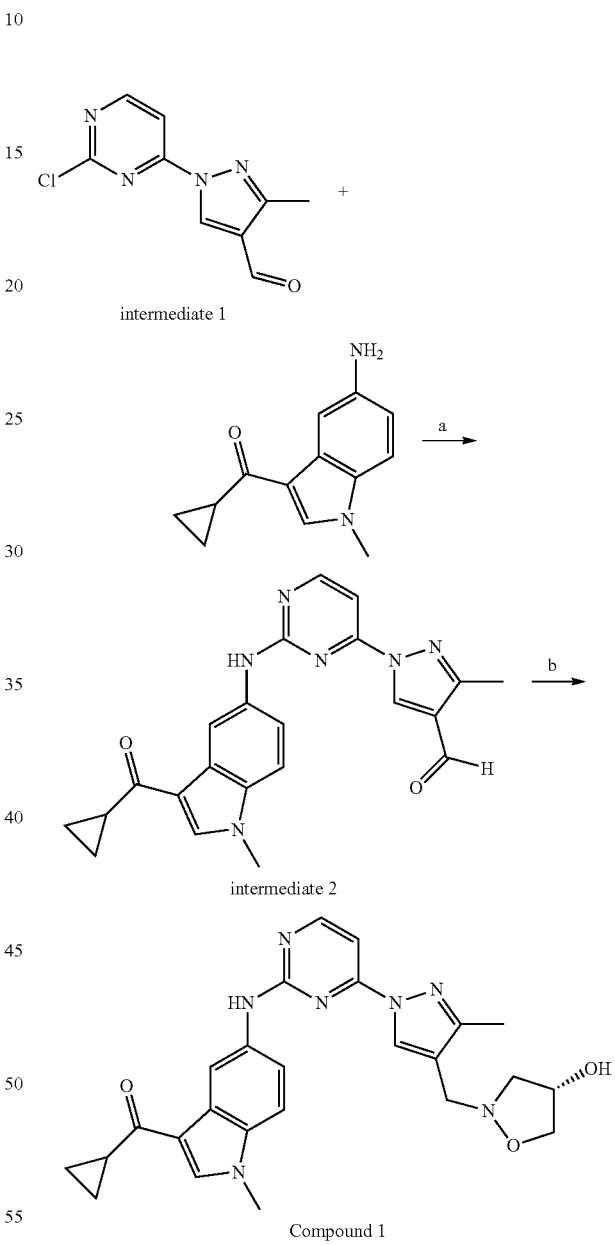

a)Pd(OAc)₂, Xantphos, K₂CO₃, Dioxane,
b) (S)-isoxazolidin-4-ol hydrochloride, NaBH(OAc)₃, Et₃N, DCM Preparation of (3-methyl-1-(2-(1-methyl-1H-indol-5-ylamino)pyrimidin-4-yl)-1H-pyrazol-4-yl)methanol; Intermediate 2

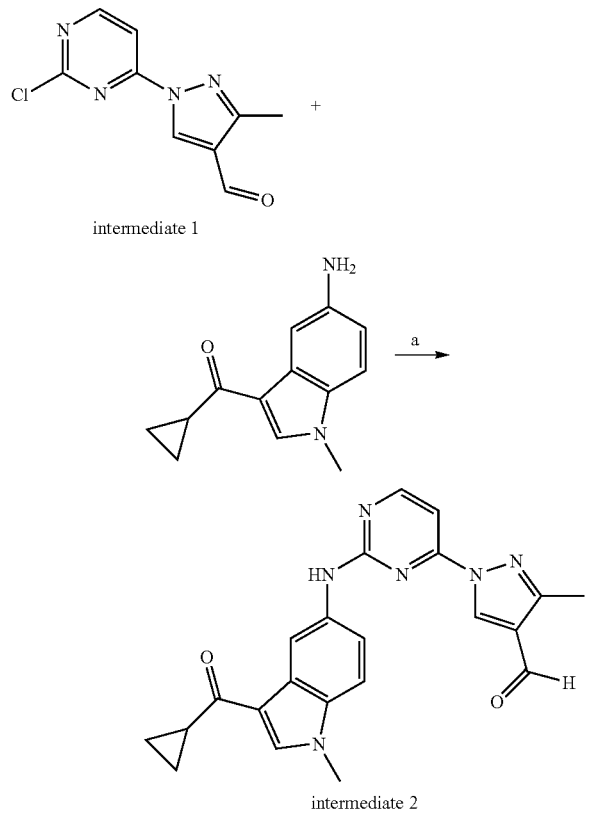

Preparation of (S)-cyclopropyl(5-(4-(4-((4-hydroxy-isoxazolidin-2-yl)methyl)-3-methyl-1H-pyrazol-1-yl)pyrimidin-2-ylamino)-1-methyl-1H-indol-3-yl)methanone; Compound 1

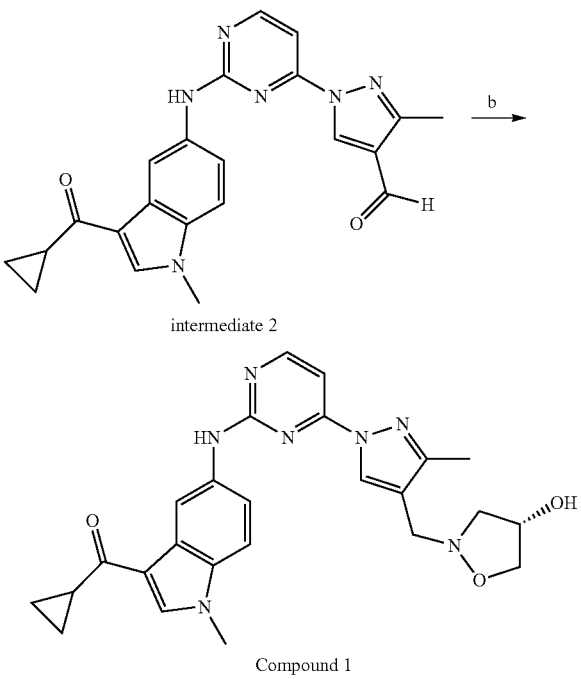

A round bottomed flask was charged with 1-(2-chloropyrimidin-4-yl)-3-methyl-1H-pyrazole-4-carbaldehyde (400 mg, 1.78 mmol), (5-amino-1-methyl-1H-indol-3-yl)(cyclopropyl)methanone (385 mg, 1.0 equiv.), potassium carbonate (0.74 g, 3.0 equiv), palladium acetate (20 mg, 0.05 equiv), (9,9-dimethyl-9H-xanthene-4,5-diyl)bis(diphenylphosphine) (Xantphos, 100 mg, 0.1 equiv.) and 40 mL of anhydrous dioxane. After being degassed by nitrogen bubbling, the reaction mixture was heated at 100° C. for 12 hours. To the reaction mixture, water was added to form solids. The resulting solids were collected by filtration, washed with water followed by ethyl acetate to give brown powder (430 mg, 60%). The collected solids were dried in vacuo and then used to next step without further purification; MS (ESI) m/z 401 [M+H]$^+$.

To a slurry of intermediate 2 (500 mg, 1.14 mmol), (S)-isoxazolidin-4-ol hydrochloride (220 mg, Tetrahedron Lett., 2006, 47, 7635-7639) and triethylamine (0.79 mL) in 10 mL of dichloromethane and 10 mL of N,N-dimethylacetamide (DMAC), was added NaBH(OAc)$_3$ (730 mg, 3.42 mmol) at room temperature. Volatiles were removed in vacuo. It was extracted with dichloromethane (×3). The collected organic layers were dried over anhydrous sodium sulfate and then concentrated in vacuo. The resulting residue was purified by silica gel chromatography (DCM/MeOH) to give 270 mg (50%) of the desired compound 1 as a pale yellow solid; MS (ESI) m/z 474 [M+H]$^+$, $^1$H NMR (300 MHz, DMSO-d$_6$) δ 9.85 (s, 1H), 9.30 (s, 1H), 9.02 (s, 1H), 8.48 (d, J=5.4 Hz, 1H), 7.47 (d, J=9.0 Hz, 1H), 7.36 (d, J=8.7 Hz, 1H), 7.13 (d, J=5.4 Hz, 1H), 5.19 (s, 1H), 4.60 (d, 1H), 4.10 (m, 1H), 3.94 (d, 2H), 3.87 (s, 3H), 3.81 (m, 1H), 2.86 (m, 1H), 2.65 (m, 1H), 2.29 (s, 1H), 0.92 (d, J=6.0 Hz, 2H).

Method 2: Preparation of (S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)-2-methylpropan-1-one; Compound 2

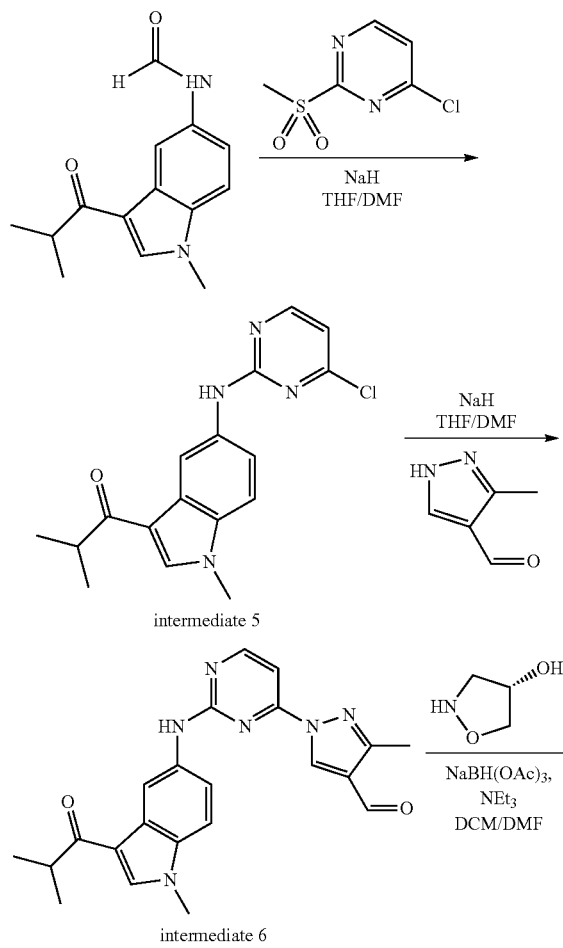

Preparation of 1-(5-(4-chloropyrimidin-2-ylamino)-1-methyl-1H-indol-3-yl)-2-methylpropan-1-one; Intermediate 5

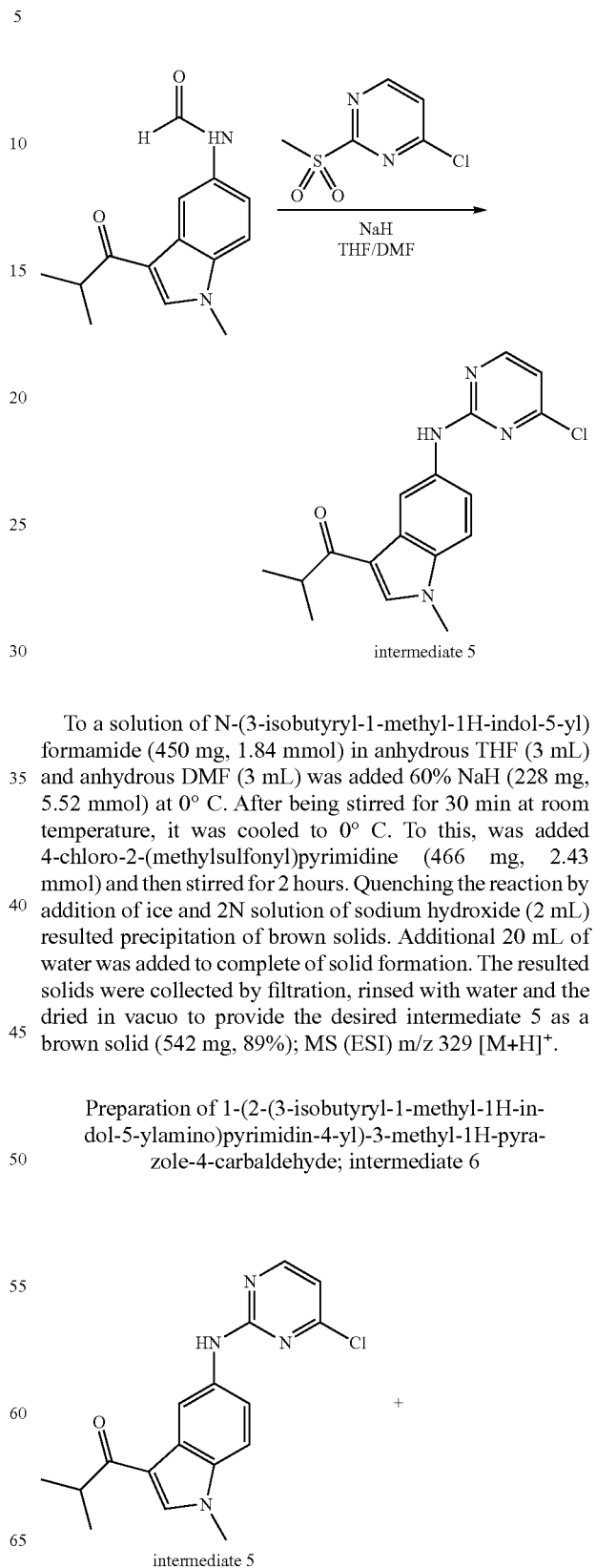

To a solution of N-(3-isobutyryl-1-methyl-1H-indol-5-yl)formamide (450 mg, 1.84 mmol) in anhydrous THF (3 mL) and anhydrous DMF (3 mL) was added 60% NaH (228 mg, 5.52 mmol) at 0° C. After being stirred for 30 min at room temperature, it was cooled to 0° C. To this, was added 4-chloro-2-(methylsulfonyl)pyrimidine (466 mg, 2.43 mmol) and then stirred for 2 hours. Quenching the reaction by addition of ice and 2N solution of sodium hydroxide (2 mL) resulted precipitation of brown solids. Additional 20 mL of water was added to complete of solid formation. The resulted solids were collected by filtration, rinsed with water and the dried in vacuo to provide the desired intermediate 5 as a brown solid (542 mg, 89%); MS (ESI) m/z 329 [M+H]$^+$.

Preparation of 1-(2-(3-isobutyryl-1-methyl-1H-indol-5-ylamino)pyrimidin-4-yl)-3-methyl-1H-pyrazole-4-carbaldehyde; intermediate 6

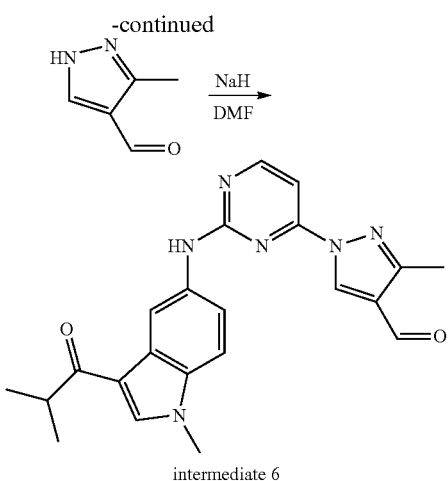

intermediate 6

To a solution of 3-methyl-1H-pyrazole-4-carbaldehyde (273 mg, 2.48 mmol) in anhydrous DMF (5 mL) was added 60% NaH (130 mg, 3.25 mmol) at 0° C. After being stirred for 30 min at room temperature, it was cooled to 0° C. To this, was added intermediate 5 (542 mg, 1.65 mmol) and then stirred for 6 hours at 60° C. Quenching the reaction by addition of ice and 20 mL of water resulted precipitation of brown solids. The resulted solids were collected by filtration, rinsed with water and the dried in vacuo to provide the desired intermediate 6 as a brown solid (424 mg, 80%); MS (ESI) m/z 403 [M+H]+.

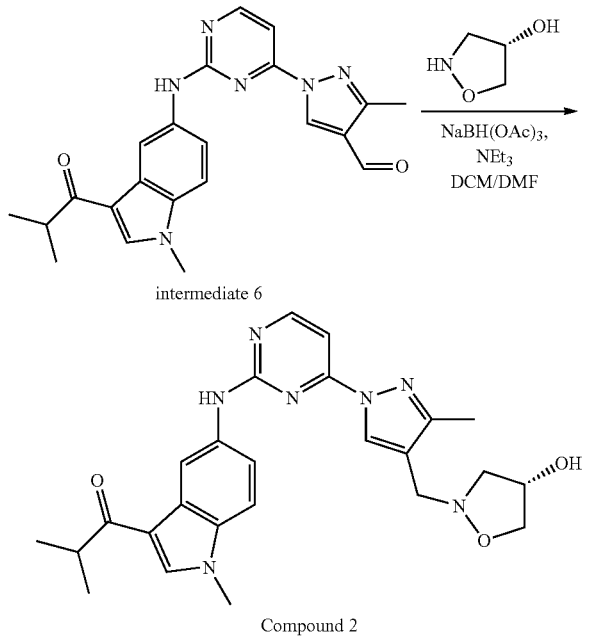

intermediate 6

Compound 2

To a slurry of Intermediate 6 (200 mg, 0.5 mmol), (S)-isoxazolidin-4-ol hydrochloride (95 mg, 0.75 mmol) and triethylamine (0.4 mL) in 10 mL of dichloromethane, was added NaBH(OAc)₃ (0.32 g, 1.5 mmol) at room temperature. The reaction was stirred for 12 hour at room temperature and then volatiles were removed in vacuo. The resulting residue was extracted with dichloromethane and washed with brine. The collected organic layer was dried over anhydrous sodium sulfate and then concentrated in vacuo. The resulting residue was purified by silica gel chromatography (DCM/MeOH) to afford the desired Compound No. 2 as a pale yellow solid (178 mg, 75%); MS (ESI) m/z 476 [M+H]+, ¹H NMR (300 MHz, CDCl₃) δ 9.21 (s, 1H), 9.01 (s, 1H), 8.41 (d, J=5.4 Hz, 1H), 7.74 (s, 1H), 7.25-7.37 (m, 3H), 4.71-4.73 (m, 1H), 4.05-4.17 (m, 3H), 3.88 (s, 3H), 3.75-3.81 (m, 1H), 3.01-3.17 (m, 1H), 2.42-3.00 (m, 1H), 2.42 (s, 3H), 1.30 (d, J=6.6 Hz, 6H).

Method 3: Preparation of 1-((1-(2-(3-chloro-1,2-dimethyl-1H-indol-5-ylamino)pyrimidin-4-yl)-3-methyl-1H-pyrazol-4-yl)methyl)azetidin-3-ol; Compound 31

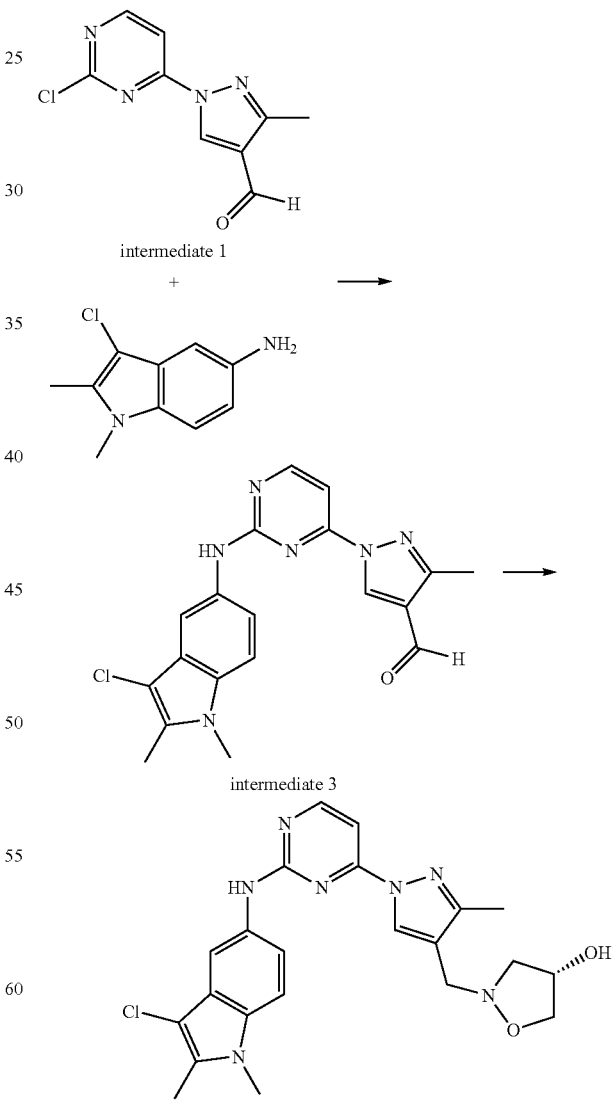

Compound No. 31

Preparation of 1-(2-(3-chloro-1,2-dimethyl-1H-indol-5-ylamino)pyrimidin-4-yl)-3-methyl-1H-pyrazole-4-carbaldehyde; Intermediate 3

A round bottomed flask was charged with 1-(2-chloropyrimidin-4-yl)-3-methyl-1H-pyrazole-4-carbaldehyde (574 mg, 2.58 mmol), 2-chloro-1,3-dimethyl-1H-indol-5-amine (502 mg, 1.0 equiv.), potassium carbonate (1.1 g, 3.0 equiv), palladium acetate (58 mg, 0.1 equiv.), Xantphos (298 mg, 0.2 equiv.) and 50 mL of anhydrous dioxane. After being degassed by nitrogen bubbling, the reaction mixture was heated at 100° C. for 3 hours. Volatiles were removed in vacuo and then the resulting residue was extracted with dichloromethane. The collected organic layer was dried over anhydrous sodium sulfate and then concentrated in vacuo. The resulting residue was purified by silica gel chromatography (DCM/MeOH) to give 467 mg (48%) of the desired intermediate 3 as a pale yellow solid; MS (ESI) m/z 381 [M+H]+.

Preparation of (S)-2-((1-(2-(3-chloro-1,2-dimethyl-1H-indol-5-ylamino)pyrimidin-4-yl)-3-methyl-1H-pyrazol-4-yl)methyl)isoxazolidin-4-ol; Compound 31

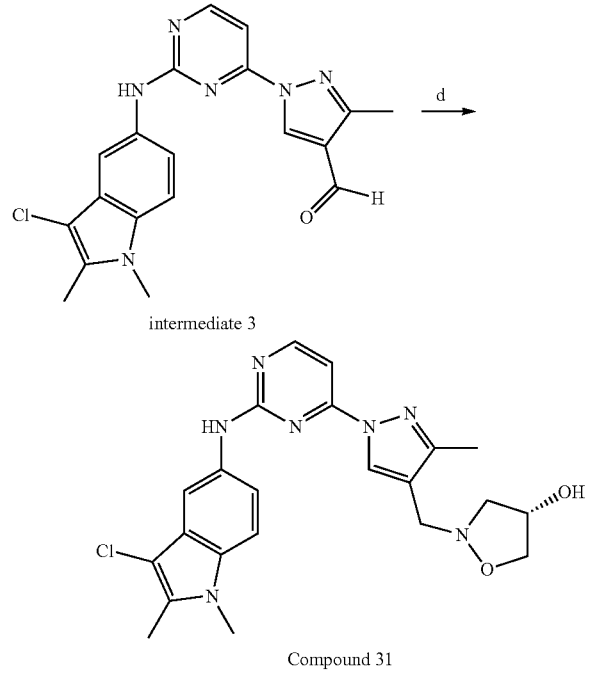

intermediate 3

Compound 31

To a slurry of Intermediate 3 (190 mg, 0.5 mmol), (S)-isoxazolidin-4-ol hydrochloride (95 mg, 0.75 mmol) and triethylamine (0.4 mL) in 10 mL of dichloromethane, was added NaBH(OAc)3 (0.32 g, 1.5 mmol) at room temperature. The reaction was stirred for 12 hour at room temperature and then quenched with 1N—NaOH. It was extracted with ethyl acetate and washed twice with brine. The collected organic layer was dried over anhydrous sodium sulfate and then concentrated in vacuo. The resulting residue was purified by silica gel chromatography (DCM/MeOH) to afford desired Compound No. 31 as a pale yellow solid (159 mg, 70%); MS (ESI) m/z 454 [M+H]+. 1H NMR (300 MHz, CDCl3) δ 8.43 (s, 1H), 8.34 (d, J=5.4 Hz, 1H), 7.89 (s, 1H), 7.68 (s, 1H), 7.14-7.16 (m, 3H), 4.73 (brs, 1H), 4.23 (brs, 1H), 3.92-3.96 (m, 2H), 3.84 (brs, 1H), 3.63 (s, 3H), 3.25 (brs, 1H), 2.73 (brs, 1H), 2.40 (s, 3H), 2.36 (s, 3H Preparation of Compound 4 to Compound 30 and Compound 32 to Compound 34

The following compounds were prepared by a method similar to that described for preparations of Compound No. 1 (Method I), Compound No. 2 (Method 2) or Compound No. 31 (method 3) using the appropriate 2-amino substituted pyrimidinyl aldehyde and the appropriate amine with or without base by reductive amination.

(S)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone; Compound 4

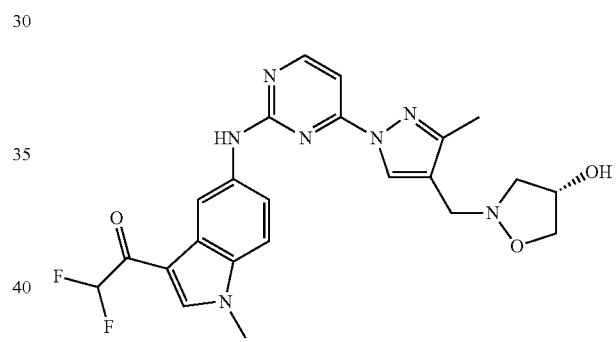

MS (ESI) m/z 484 [M+H]+.

(S)-ethyl 3-acetyl-5-(4-(4-((4-hydroxyisoxazolidin-2-yl)methyl)-3-methyl-1H-pyrazol-1-yl)pyrimidin-2-ylamino)-1H-indole-1-carboxylate; Compound 5

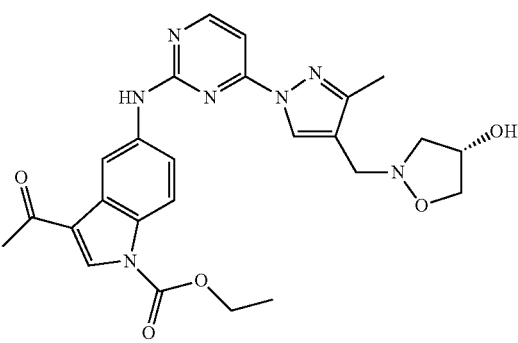 [SMILES: CCOC(=O)n1cc(C(C)=O)c2cc(Nc3nccc(-n4cc(CN5C[C@H](O)CO5)c(C)n4)n3)ccc21]

MS (ESI) m/z 505 [M+H]+.

41

(S)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone; Compound 6

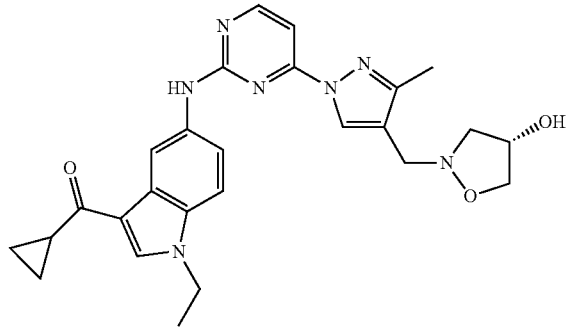 [SMILES: CCn1cc(C(=O)C2CC2)c2cc(Nc3nccc(-n4cc(CN5C[C@H](O)CO5)c(C)n4)n3)ccc21]

MS m/z: 488 (M+H)$^+$, $^1$H NMR (300 MHz, CDCl$_3$) δ 9.19 (brs, 1H), 8.96 (brs, 1H), 8.38 (d, J=5.4 Hz, 1H), 7.89 (s, 1H), 7.63 (s, 1H), 7.20-7.31 (m, 1H), 4.68-4.72 (m, 1H), 4.21 (q, J=7.2 Hz, 2H), 4.06-4.10 (m, 2H), 3.93-3.99 (m, 1H), 3.78-3.80 (m, 1H), 3.19-3.24 (m, 1H), 2.95-2.97 (m, 1H), 2.42-2.46 (m, 1H), 2.39 (s, 3H), 1.56 (t, J=7.2 Hz, 3H), 1.20-1.27 (m, 2H), 0.92-0.96 (m, 2H).

(S)-2,2,2-trifluoro-1-(5-(4-(4-((4-hydroxyisoxazolidin-2-yl)methyl)-3-methyl-1H-pyrazol-1-yl)pyrimidin-2-ylamino)-1H-indol-3-yl)ethanone; Compound 7

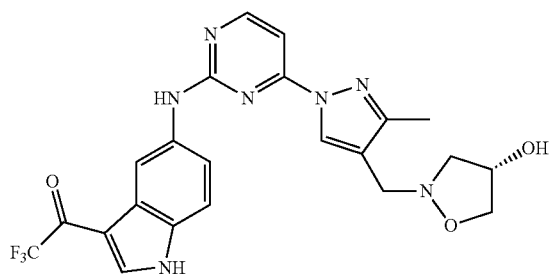 [SMILES: Cc1nn(-c2ccnc(Nc3ccc4[nH]cc(C(=O)C(F)(F)F)c4c3)n2)cc1CN1C[C@H](O)CO1]

MS m/z: 488 (M+H)$^+$, $^1$H NMR (300 MHz, DMSO-d$_6$) δ 9.93 (s, 1H), 9.17 (s, 1H), 8.87 (s, 1H), 8.52 (d, J=5.4 Hz, 1H), 8.41 (s, 1H), 7.53 (d, 2H), 7.17 (d, J=5.4 Hz, 1H), 5.16 (s, 1H), 4.60 (s, 1H), 4.07 (brs, 1H), 3.90 (m, 2H), 3.82 (s, 1H), 2.88 (s, 1H), 2.73 (m, 1H), 2.29 (s, 3H).

42

(S)-cyclopropyl(5-(4-(4-((4-hydroxyisoxazolidin-2-yl)methyl)-3-methyl-1H-pyrazol-1-yl)pyrimidin-2-ylamino)-1-isopropyl-1H-indol-3-yl)methanone; Compound 8

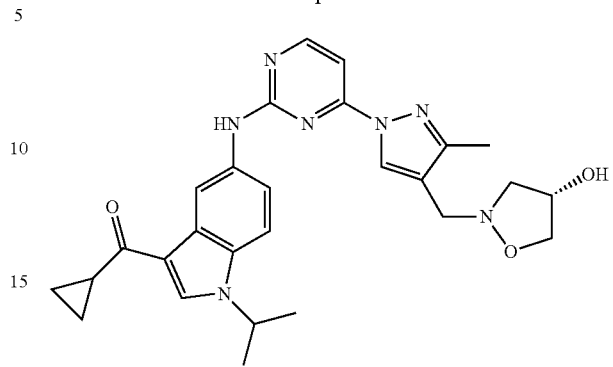

MS m/z: 502 (M+11)$^+$, $^1$H NMR (300 MHz, DMSO-d$_6$) δ 9.81 (s, 1H), 9.28 (s, 1H), 9.01 (s, 1H), 8.63 (s, 1H), 8.48 (d, J=5.4 Hz, 1H), 7.56 (d, J=8.7 Hz, 1H), 7.35 (d, J=7.8 Hz, 1H), 7.13 (d, J=5.4 Hz, 1H), 5.10-5.31 (m, 1H), 4.79-4.83 (m, 1H), 4.59-4.65 (m, 1H), 3.91 (d, J=12.6 Hz, 2H), 3.20-3.30 (m, 1H), 2.71-2.90 (m, 1H), 2.70 (s, 2H), 2.29 (s, 3H, CH$_3$), 1.55 (d, J=6.6 Hz, 6H), 1.02-1.04 (m, 2H), 0.90-0.92 (m, 2H).

(S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone; Compound 9

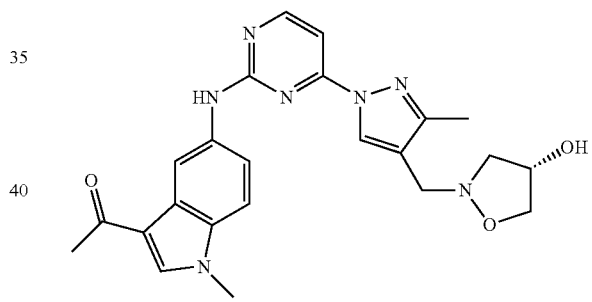

MS m/z: 448 (M+H)$^+$.

(R)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone; Compound 10

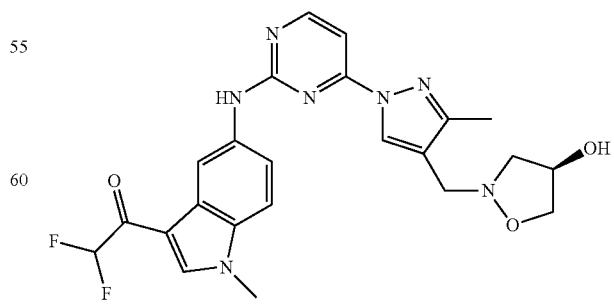

MS m/z: 484 (M+H)$^+$.

(R)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone; Compound 11

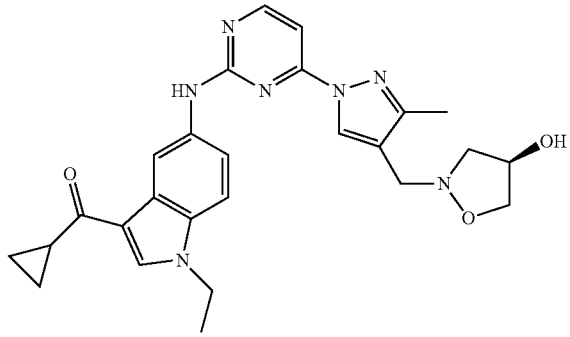 [SMILES: CCn1cc(C(=O)C2CC2)c2cc(Nc3nccc(-n4cc(CN5C[C@@H](O)CO5)c(C)n4)n3)ccc21]

MS m/z: 488 (M+H)+, 1H NMR (300 MHz, CDCl3) δ 9.16 (brs, 1H), 8.94 (brs, 1H), 8.39 (d, J=5.4 Hz, 1H), 7.89 (s, 1H), 7.54 (s, 1H), 7.21-7.54 (m, 2H), 4.71 (brs, 1H), 4.22 (q, J=7.5 Hz, 2H), 4.06-4.11 (m, 2H), 3.98 (brs, 1H), 3.76-3.78 (m, 1H), 3.19 (brs, 1H), 2.81-2.89 (m, 1H), 2.44-2.47 (m, 1H), 2.39 (s, 3H), 1.57 (t, J=7.5 Hz, 2H), 1.20-1.25 (m, 2H), 0.92-0.96 (m, 2H).

(S)-cyclopropyl(5-(4-(4-((4-hydroxyisoxazolidin-2-yl)methyl)-3-methyl-1H-pyrazol-1-yl)pyrimidin-2-ylamino)-1H-indol-3-yl)methanone; Compound 12

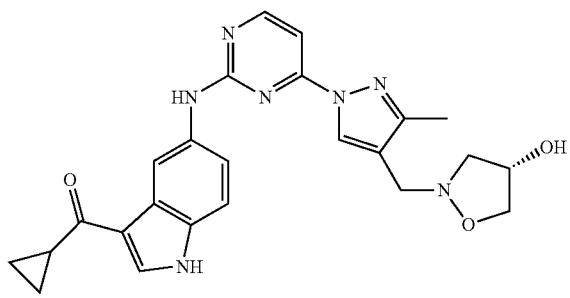 [SMILES: Cc1nn(-c2ccnc(Nc3ccc4[nH]cc(C(=O)C5CC5)c4c3)n2)cc1CN1C[C@H](O)CO1]

MS m/z: 460 (M+H)+. 1H NMR (300 MHz, DMSO-d6) δ 12.00 (s, 1H), 9.98 (s, 1H), 9.12 (s, 2H), 8.53 (d, J=5.4 Hz, 1H), 7.42 (m, 2H), 7.18 (d, J=5.4 Hz, 1H), 4.80 (s, 1H), 4.54 (m, 1H), 4.21 (m, 2H), 4.02 (s, 1H), 3.58 (s, 1H), 2.77 (d, 1H), 2.68 (m, 1H), 2.36 (s, 3H), 1.04 (m, 2H), 0.90 (s, 2H).

cyclopropyl(1-ethyl-5-(4-(4-((4-hydroxy-4-methylisoxazolidin-2-yl)methyl)-3-methyl-1H-pyrazol-1-yl)pyrimidin-2-ylamino)-1H-indol-3-yl)methanone; Compound 13

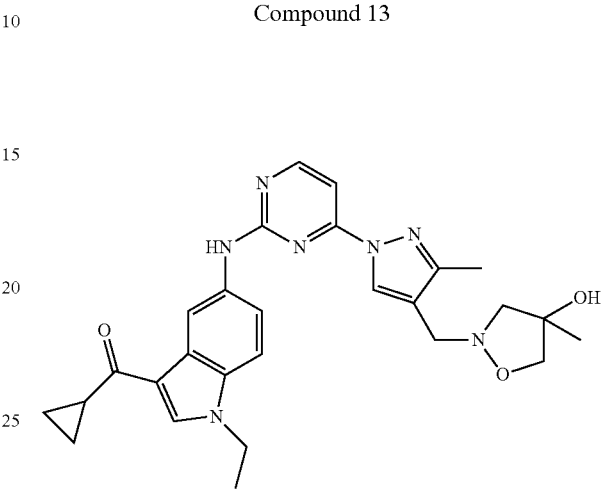

MS m/z: 502 (M+H)+. 1H NMR (300 MHz, CDCl3) δ 9.20 (brs, 1H), 8.97 (brs, 1H), 8.40 (d, J=5.7 Hz, 1H), 7.91 (s, 1H), 7.43 (s, 1H), 7.22-7.34 (m, 2H), 4.24 (q, J=7.5 Hz, 2H), 4.10-4.14 (m, 2H), 3.87 (brs, 2H), 3.10-3.17 (m, 1H), 2.97-3.02 (m, 1H), 2.44-2.50 (m, 1H), 2.40 (s, 3H), 1.58 (t, J=7.5 Hz, 3H), 1.45 (s, 3H), 1.27-1.29 (m, 2H), 0.93-0.98 (m, 2H).

cyclopropyl(5-(4-(4-((4-hydroxy-4-methylisoxazolidin-2-yl)methyl)-3-methyl-1H-pyrazol-1-yl)pyrimidin-2-ylamino)-1-methyl-1H-indol-3-yl)methanone; Compound 14

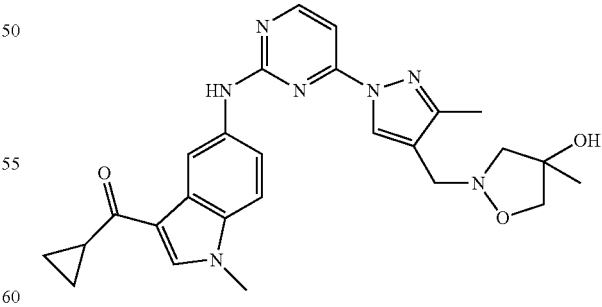

MS m/z: 488 (M+H)+. 1H NMR (300 MHz, CDCl3) δ 9.23 (brs, 1H), 8.99 (brs, 1H), 8.37 (d, J=5.4 Hz, 1H), 7.83 (s, 1H), 7.34 (s, 1H), 7.21-7.26 (m, 2H) 3.99-4.14 (m, 4H), 3.86 (s, 3H), 3.16-3.19 (m, 1H), 2.60-2.71 (m, 1H), 2.44-2.47 (m, 1H), 2.40 (s, 3H), 1.45 (s, 3H), 1.17-1.26 (m, 2H), 0.92-0.96 (m, 2H).

45

(S)-cyclopropyl(5-(4-(4-((4-hydroxyisoxazolidin-2-yl)methyl)-3-methyl-1H-pyrazol-1-yl)pyrimidin-2-ylamino)-1-(2,2,2-trifluoroethyl)-1H-indol-3-yl)methanone; Compound 15

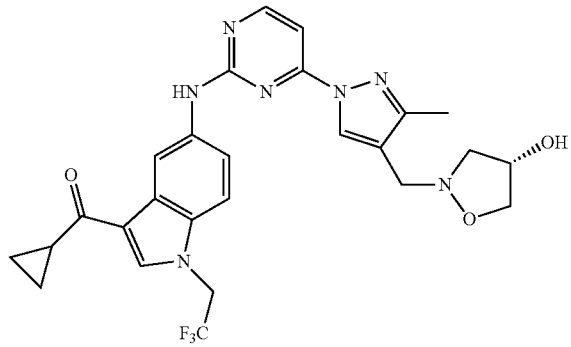 [SMILES: Cc1nn(-c2ccnc(Nc3ccc4c(c3)c(C(=O)C3CC3)cn4CC(F)(F)F)n2)cc1CN1C[C@H](O)CO1]

MS m/z: 542 (M+H)$^+$. $^1$H NMR (300 MHz, DMSO-d$_6$) δ 9.86 (s, 1H), 9.27 (s, 1H), 8.97 (s, 1H), 8.56 (s, 1H), 8.50 (d, J=5.4 Hz, 1H), 7.65 (d, J=8.7 Hz, 1H), 7.41 (d, J=9.0 Hz, 1H), 7.16 (d, J=5.4 Hz, 1H), 5.32 (m, 2H), 5.14 (s, 1H), 4.60 (s, 1H), 4.08 (s, 1H), 3.93 (m, 2H), 3.82 (s, 1H), 2.88 (s, 1H), 2.59 (m, 1H), 2.30 (s, 3H), 1.08 (m, 2H), 0.98 (m, 2H).

cyclopropyl(5-(4-(4-((4-hydroxy-4-methylisoxazolidin-2-yl)methyl)-3-methyl-1H-pyrazol-1-yl)pyrimidin-2-ylamino)-1-(2,2,2-trifluoroethyl)-1H-indol-3-yl)methanone; Compound 16

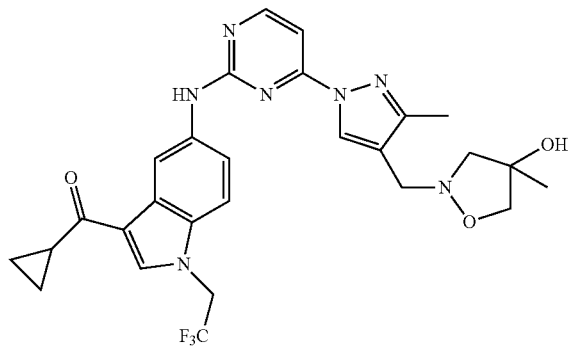 [SMILES: Cc1nn(-c2ccnc(Nc3ccc4c(c3)c(C(=O)C3CC3)cn4CC(F)(F)F)n2)cc1CN1CC(C)(O)CO1]

MS m/z: 556 (M+H)$^+$. $^1$H NMR (300 MHz, DMSO-d$_6$) δ 9.87 (s, 1H), 9.29 (s, 1H), 9.00 (s, 1H), 8.56 (s, 1H), 8.50 (d, J=5.4 Hz, 1H), 7.65 (d, J=8.7 Hz, 1H), 7.41 (d, J=9.0 Hz, 1H), 7.15 (d, J=5.4 Hz, 1H), 5.35 (m, 2H), 5.05 (s, 1H), 3.97 (m, 2H), 3.89 (brs, 1H), 3.62 (brs, 1H), 3.00 (brs, 1H), 2.67 (m, 1H), 2.30 (s, 3H), 1.32 (s, 3H), 1.09 (s, 2H), 0.95 (m, 2H).

46

(S)-1-(5-(5-chloro-4-(4-((4-hydroxyisoxazolidin-2-yl)methyl)-3-methyl-1H-pyrazol-1-yl)pyrimidin-2-ylamino)-1-methyl-1H-indol-3-yl)-2,2,2-trifluoroethanone; Compound 17

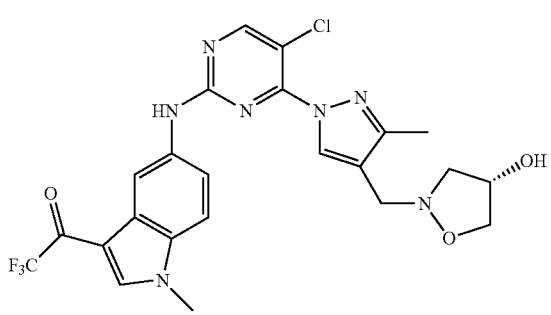 [SMILES: Cc1nn(-c2nc(Nc3ccc4c(c3)c(C(=O)C(F)(F)F)cn4C)ncc2Cl)cc1CN1C[C@H](O)CO1]

MS m/z: 536 (M+H)$^+$.

(S)-2,2,2-trifluoro-1-(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)ethanone; Compound 18

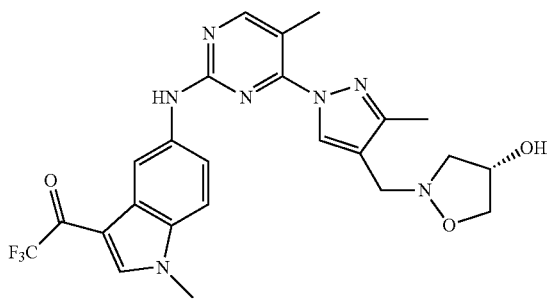 [SMILES: Cc1cnc(Nc2ccc3c(c2)c(C(=O)C(F)(F)F)cn3C)nc1-n1cc(CN2C[C@H](O)CO2)c(C)n1]

MS m/z: 516 (M+H)$^+$.

(S)-cyclopropyl(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)methanone; Compound 19

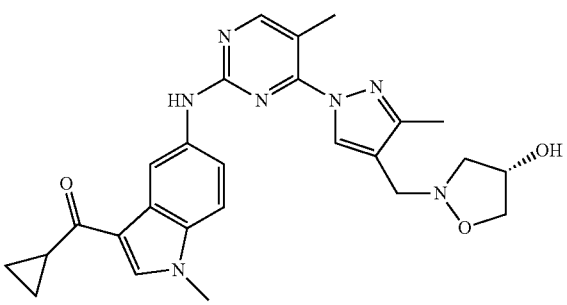 [SMILES: Cc1cnc(Nc2ccc3c(c2)c(C(=O)C2CC2)cn3C)nc1-n1cc(CN2C[C@H](O)CO2)c(C)n1]

MS m/z: 488 (M+H)$^+$.

47

(S)-cyclopropyl(1-ethyl-5-(5-fluoro-4-(4-((4-hydroxyisoxazolidin-2-yl)methyl)-3-methyl-1H-pyrazol-1-yl)pyrimidin-2-ylamino)-1H-indol-3-yl)methanone; Compound 20

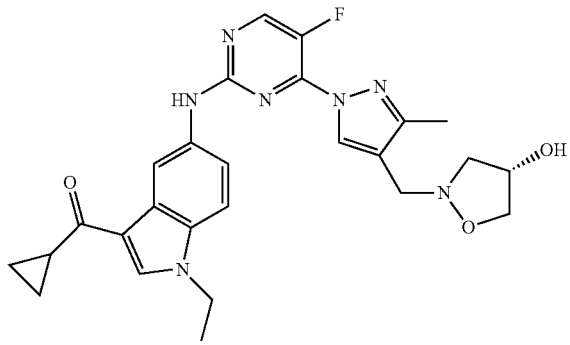 [SMILES: CCn1cc(C(=O)C2CC2)c2cc(Nc3ncc(F)c(-n4cc(CN5C[C@H](O)CO5)c(C)n4)n3)ccc21]

MS m/z: 506 (M+H)⁺.

(S)-cyclopropyl(1-ethyl-5-(5-fluoro-4-(3-((4-hydroxyisoxazolidin-2-yl)methyl)-4-methyl-1H-pyrrol-1-yl)pyrimidin-2-ylamino)-1H-indol-3-yl)methanone; Compound 21

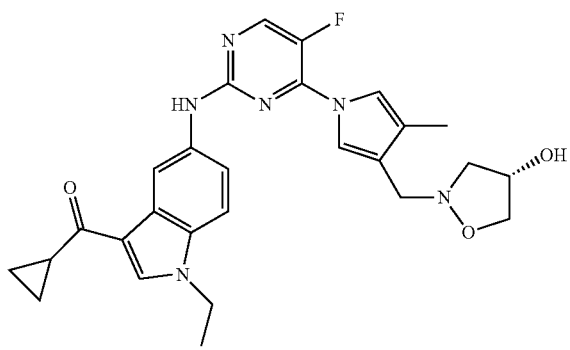 [SMILES: CCn1cc(C(=O)C2CC2)c2cc(Nc3ncc(F)c(-n4cc(C)c(CN5C[C@H](O)CO5)c4)n3)ccc21]

MS m/z: 505 (M+H)⁺.

(S)-cyclopropyl(1-ethyl-5-(4-(4-((4-hydroxyisoxazolidin-2-yl)methyl)-3-methyl-1H-pyrazol-1-yl)-5-methylpyrimidin-2-ylamino)-1H-indol-3-yl)methanone; Compound 22

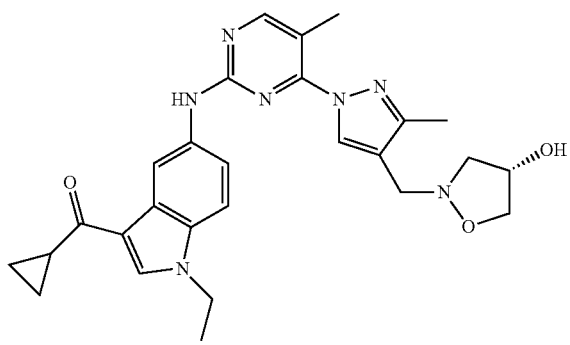 [SMILES: CCn1cc(C(=O)C2CC2)c2cc(Nc3ncc(C)c(-n4cc(CN5C[C@H](O)CO5)c(C)n4)n3)ccc21]

MS m/z: 502 (M+H)⁺.

48

(S)-cyclopropyl(1-(2-fluoroethyl)-5-(4-(4-((4-hydroxyisoxazolidin-2-yl)methyl)-3-methyl-1H-pyrazol-1-yl)pyrimidin-2-ylamino)-1H-indol-3-yl)methanone; Compound 23

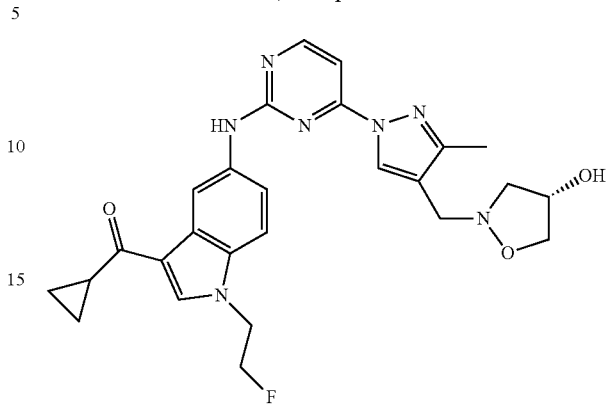

MS m/z: 506 (M+H)⁺.

cyclopropyl(1-(2-fluoroethyl)-5-(4-(4-(((S)-4-hydroxyisoxazolidin-2-yl)methyl)-3-methyl-1H-pyrazol-1-yl)pyrimidin-2-ylamino)indolin-3-yl)methanone; Compound 24

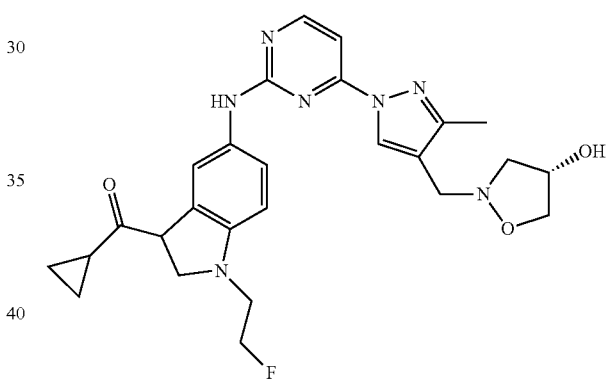

MS m/z: 508 (M+H)⁺.

(S)-cyclopropyl(5-(4-(3-cyclopropyl-4-((4-hydroxyisoxazolidin-2-yl)methyl)-1H-pyrazol-1-yl)pyrimidin-2-ylamino)-1-ethyl-1H-indol-3-yl)methanone; Compound 25

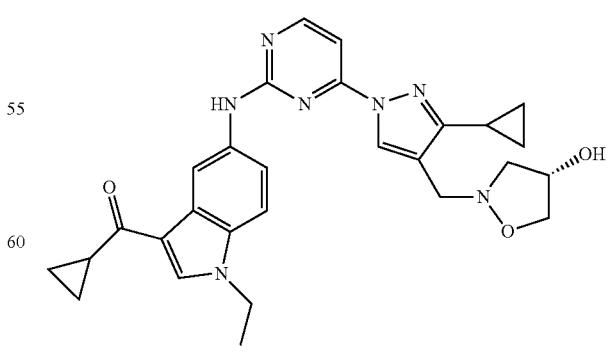

MS m/z: 514 (M+H)⁺. ¹H NMR (300 MHz, CDCl₃) δ 9.14 (s, 1H) 8.97 (s, 1H) 8.37 (d, J=5.4 Hz, 1H) 7.92 (s, 1H), 7.20-7.38 (m, 4H) 4.60-4.70 (m, 1H) 4.17-4.29 (m, 4H) 4.04-4.10 (m, 1H) 3.80-3.88 (m, 1H) 3.19-3.23 (m, 1H) 2.84-2.90 (m, 1H) 2.40-2.50 (m, 2H) 1.58-1.61 (m, 3H) 1.25-1.30 (m, 2H) 0.93-0.98 (m, 6H).

(S)-2-((3-methyl-1-(2-(1-methyl-3-(methylsulfonyl)-1H-indazol-5-ylamino)pyrimidin-4-yl)-1H-pyrazol-4-yl)methyl)isoxazolidin-4-ol; Compound 26

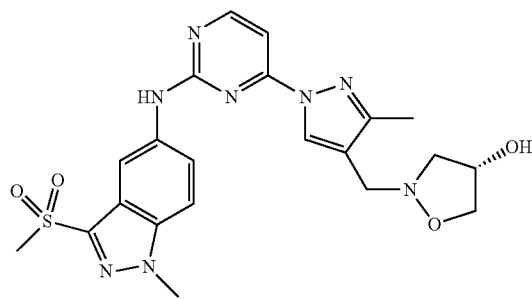 [SMILES: Cc1nn(-c2ccnc(Nc3ccc4c(c3)c(S(C)(=O)=O)nn4C)n2)cc1CN1C[C@H](O)CO1]

MS m/z: 485 (M+H)+.
$^1$H NMR (300 MHz, DMSO-d$_6$) δ 10.10 (s, 1H), 8.90 (s, 1H), 8.66 (s, 1H), 8.55 (d, J=5.7 Hz, 1H), 7.81 (d, J=9.3 Hz), 7.67 (d, J=9.3 Hz, 1H), 7.21 (d, J=5.4 Hz, 1H), 5.25 (brs, 1H), 4.64 (s, 1H), 4.18 (s, 3H), 4.17 (brs, 1H), 3.87 (m, 2H), 3.35 (s, 3H), 2.88 (s, 1H), 2.29 (s, 3H).

(S)-cyclopropyl(5-(4-(4-((4-hydroxyisoxazolidin-2-yl)methyl)-3-methyl-1H-pyrazol-1-yl)pyrimidin-2-ylamino)-1-(methylsulfonyl)-1H-indol-3-yl)methanone; Compound 27

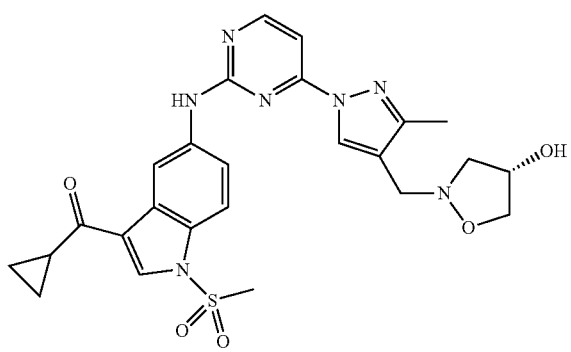 [SMILES: Cc1nn(-c2ccnc(Nc3ccc4c(c3)c(C(=O)C3CC3)cn4S(C)(=O)=O)n2)cc1CN1C[C@H](O)CO1]

MS m/z: 538 (M+H)+. $^1$H NMR (300 MHz, DMSO-d$_6$) δ 10.02 (s, 1H), 9.32 (s, 1H), 8.96 (s, 1H), 8.71 (s, 1H), 8.52 (d, J=5.4 Hz, 1H), 7.82 (d, J=9.0 Hz, 1H), 7.75 (d, J=9.0 Hz, 1H), 7.19 (d, J=5.4 Hz, 1H), 5.21 (s, 1H), 4.61 (s, 1H), 4.11 (s, 1H), 3.92 (d, 2H), 3.64 (s, 3H), 2.98 (s, 1H), 2.70 (m, 1H), 2.29 (s, 3H), 1.12 (m, 2H), 1.02 (m, 2H).

cyclopropyl(5-(4-(4-((4-hydroxy-4-methylmorpholino)methyl)-1H-pyrazol-1-yl)pyrimidin-2-ylamino)-1-methyl-1H-indol-3-yl)methanone; Compound 28

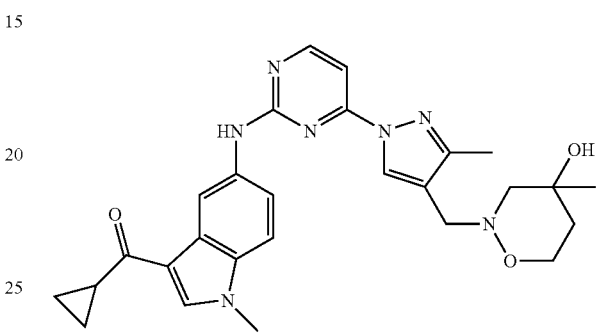

MS m/z: 502 (M+H)+. $^1$H NMR (300 MHz, CDCl$_3$) δ 8.89 (s, 1H), 8.75 (s, 1H), 8.31 (d, J=5.7 Hz, 1H), 7.85 (s, 1H), 7.37-7.40 (m, 2H), 7.16 (d, J=5.7 Hz, 1H), 4.00-4.08 (m, 1H), 3.85 (s, 3H) 3.70-3.79 (m, 3H), 3.50 (d, J=10.8 Hz, 1H), 3.32 (d, J=10.8 Hz, 1H), 2.40-2.47 (m, 1H), 2.35 (s, 3H), 2.18-2.27 (m, 1H), 2.04-2.14 (m, 1H), 1.31 (s, 3H), 1.16-1.20 (m, 2H), 0.89-0.93 (m, 2H).

(S)-cyclopropyl(1-ethyl-5-(4-(3-((4-hydroxyisoxazolidin-2-yl)methyl)-4-methyl-1H-pyrrol-1-yl)pyrimidin-2-ylamino)-1H-indol-3-yl)methanone; Compound 29

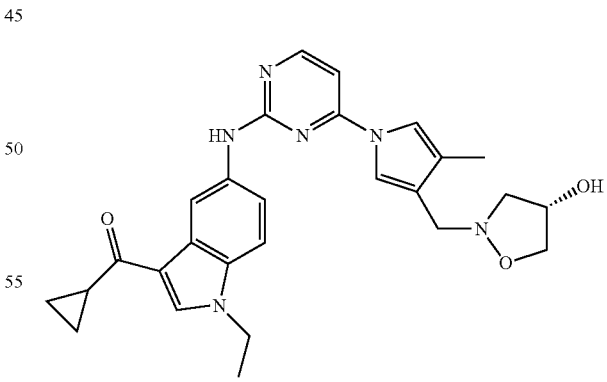

MS m/z: 487 (M+H)+. $^1$H NMR (300 MHz, CDCl$_3$) δ 8.94 (s, 1H), 8.30 (d, J=5.7 Hz, 1H), 7.91 (s, 1H), 7.63 (s, 1H), 7.39-7.41 (m, 2H), 7.30-7.35 (m, 2H), 6.58 (d, J=5.7 Hz, 1H), 4.71 (brs, 1H), 4.25 (q, J=7.2 Hz, 2H), 4.13-4.15 (m, 2H), 3.79-3.85 (m, 2H), 3.20 (brs, 1H), 2.85 (brs, 1H), 2.41-2.48 (m, 1H), 2.17 (s, 3H), 1.58 (t, J=7.2 Hz, 3H), 1.26-1.28 (m, 2H), 0.88-0.96 (m, 2H).

51

(S)-cyclopropyl(5-(4-(4-((4-hydroxyisoxazolidin-2-yl)methyl)-1H-pyrazol-1-yl)pyrimidin-2-ylamino)-1-methyl-1H-indol-3-yl)methanone; Compound 30

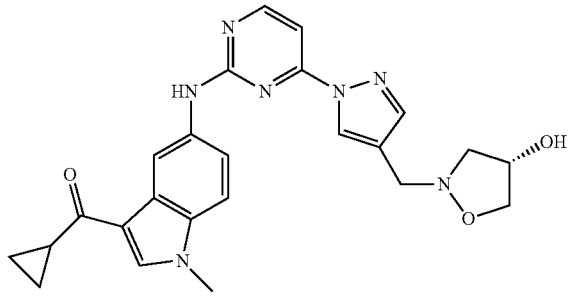 [SMILES: Cn1cc(C(=O)C2CC2)c2cc(Nc3nccc(-n4cc(CN5C[C@H](O)CO5)cn4)n3)ccc21]

MS m/z: 460 (M+H)$^+$. $^1$H NMR (300 MHz, CDCl$_3$) δ 9.21 (s, 1H), 9.05 (s, 1H), 8.42 (d, J=5.4 Hz, 1H), 7.83 (d, J=8.7 Hz, 2H), 7.38 (s, 1H), 7.30 (d, J=5.7 Hz, 1H), 7.28 (d, J=8.4 Hz, 1H), 7.22 (s, 1H) 4.70 (s, 1H), 4.25 (brs, 1H), 4.23 (d, 2H), 4.10 (brs, 1H), 3.87 (s, 3H), 3.19 (brs, 1H), 2.82 (s, 1H), 2.46 (m, 1H), 1.24 (d, 2H), 0.92 (m, 2H).

(S)-cyclopropyl(1-(2-fluoroethyl)-5-(4-(4-((4-hydroxyisoxazolidin-2-yl)methyl)-1H-pyrazol-1-yl)pyrimidin-2-ylamino)-1H-indol-3-yl)methanone; Compound 32

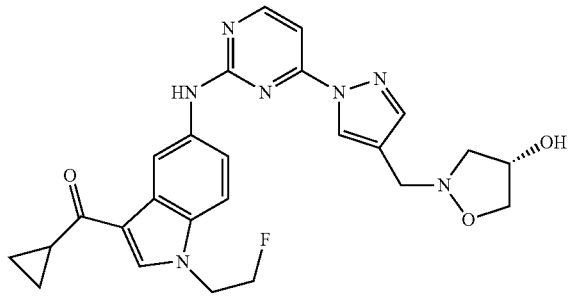 [SMILES: O=C(c1cn(CCF)c2ccc(Nc3nccc(-n4cc(CN5C[C@H](O)CO5)cn4)n3)cc12)C1CC1]

MS m/z: 492 (M+H)$^+$.

(S)-cyclopropyl(1-(2,2-difluoroethyl)-5-(4-(4-((4-hydroxyisoxazolidin-2-yl)methyl)-1H-pyrazol-1-yl)pyrimidin-2-ylamino)-1H-indol-3-yl)methanone; Compound 33

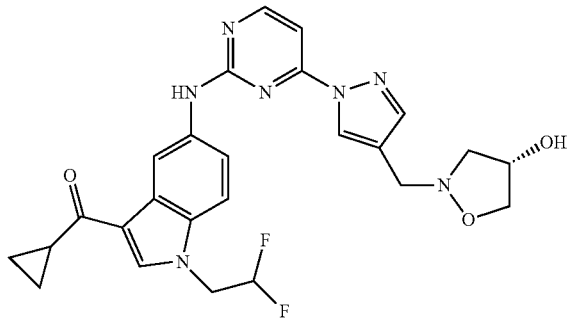 [SMILES: O=C(c1cn(CC(F)F)c2ccc(Nc3nccc(-n4cc(CN5C[C@H](O)CO5)cn4)n3)cc12)C1CC1]

MS m/z: 510 (M+H)$^+$.

52

(S)-cyclopropyl(5-(4-(4-((4-hydroxyisoxazolidin-2-yl)methyl)-1H-pyrazol-1-yl)pyrimidin-2-ylamino)-1-(2,2,2-trifluoroethyl)-1H-indol-3-yl)methanone; Compound 34

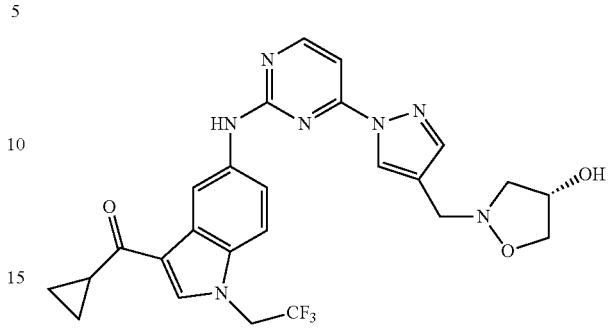

MS m/z: 528 (M+H)$^+$.

Biological Assays

1. Kinase Inhibition Assay

Compounds of the present invention were assayed to measure their capacity to inhibit a spleen tyrosine kinase (SYK).

Spleen tyrosine kinase (SYK) is a member of the SYK family of tyrosine kinases which are non-receptor cytoplasmic tyrosine kinases sharing a characteristic dual SH2 domain separated by a linker domain. SYK plays a role in transmitting signals from a variety of cell surface receptors including CD74, Fc Receptor, and integrins. Abnormal function of SYK has been implicated in instances of rheumatoid arthritis, systemic lupus erythematosus (SLE) and hematopoietic malignancies such as non-Hodgkin lymphoma including diffuse large B cell lymphoma. Several transforming viruses, such as Epstein Barr virus, bovine leukemia virus, and mouse mammary tumor virus, are known to contain "Immunoreceptor Tyrosine Activation Motifs" (ITAMs) that lead to activation of SYK.

Methods

Inhibition of Enzymatic SYK Kinase Activity

Compounds of the invention were initially diluted to 10 mM in 100% DMSO (CALBIOCHEM™) for storage and made into kinase buffer solution to create a compound concentration ranging from 1 uM and 10 uM. Serial dilutions of compounds of the invention were dispensed into a 96-well plate (GREINER BIOSCIENCES™) at 6 μL each. Purified full-length human SYK (CARNA BIOSCIENCES™) were diluted in kinase buffer and added to the compound solutions and pre-incubated for 30 minutes at room temperature. Next, ATP (TEKNOVA™) of Km (15 uM) and substrate solution (suggested manufacture substrates of PerkinElmer™, Ulight™-TK peptide for SYK) was added (12 μL each) to the wells containing the compound solution and enzyme. The reaction mixture was incubated for 1 hour. Following the incubation, the stop solution made with EDTA, water, and Lance detection buffer (PERKINELMER™) was added (12 μL each) to stop phosphorylation. Following the addition of the stop solution and 5 minutes of shaking, the detection solution containing the Europium-labeled antibody (suggested manufacture substrates of PerkinElmer™, PT66 for SYK), water, and Lance detection buffer was added (12 μL each) to the reaction mixture and incubated again for 50 minutes. Substrate phosphorylation was a function of the 665 nm emission measured following the addition of the detection solution and 50 minutes of incubation.

Results

Compounds of Formula (I) exhibited useful pharmacological properties. As used herein, an way to describe potency of inhibitory activity (nM)) is a value of inhibitory activity at 50% ($IC_{50}$). Reference compound, R406 (active form of R788, Rigel Pharmaceutical Inc.) was used for SYK to judge inhibitory activity of compounds of Formula (I).

Table 2 illustrates the inhibition of SYK by the representative compounds of Formula (I).

TABLE 2

Inhibition Activity of SYK

| Compound Number | IC50 (nM) |
|---|---|
| R406 | 23.62 |
| 1 | 6.15 |
| 2 | 8.63 |
| 3 | 2.82 |
| 4 | 9.42 |
| 5 | 45.56 |
| 6 | 4.69 |
| 7 | 8.28 |
| 8 | 7.37 |
| 9 | 13.33 |
| 10 | 24.43 |
| 11 | 6.28 |
| 12 | 13.53 |
| 13 | 17.3 |
| 14 | 41.72 |
| 15 | 2.98 |
| 16 | 14.21 |
| 17 | 131.7 |
| 18 | 159.4 |
| 19 | 271.2 |
| 20 | 66.23 |
| 21 | 230.1 |
| 22 | 79.32 |
| 23 | 3.71 |
| 24 | 3.10 |
| 25 | 5.85 |
| 26 | 87.1 |
| 27 | 5.89 |
| 28 | 106.1 |
| 29 | 69.5 |
| 30 | 2.46 |
| 31 | 26.71 |
| 32 | 3.52 |
| 33 | 5.34 |
| 34 | 5.80 |

As shown in Table 2, reference compound, R406, is multi potent, suggesting there is no selectivity across kinase whereas compounds of the present invention show better potency and better selectivity than R406.

2. Tumor Necrosis Factor (TNF)-α Release Assay

In order to address cellular potency of Compounds of Formula (I), TNF-a production was measured on treatment of a series of concentration of SYK inhibitor in THP-1 cells. The experiment indicates how well SYK inhibitor potently inhibits its target SYK kinase in cell, leading to inhibition of inflammatory cytokines including TNFa causing various inflammatory diseases and other diseases.

Methods

For SYK-dependent TNF-α release assay (i.e., via IgG stimulation), THP-1 cells derived from human monocytic cells were obtained from the American Type Culture Collection (ATCC, Manassas, Va.). This cell line was maintained with a Roswell Park Memorial Institute (RPMI) medium (GIBCO) containing 10% fetal bovine serum (FBS; GIBCO) and 0.05 mM solution of 2-mercaptoethanol. The THP-1 cells were seeded at $1 \times 10^5$ cells/100 μL/well into human IgG (10 ng/well, INVITROGEN)-coated 96 well culture plate, and serially diluted compound was then added. After an 18 hours of incubation period at 37° C., supernatants were collected for the determination of the TNF-α level by enzyme-linked immunosorbent assay (ELISA), and the remaining cells were subjected to an MTT (yellow tetrazolium salt) assay to determine the cytotoxic effects of the compound. The $IC_{50}$ value of the test compound was calculated at Gradpad Prism 5 unless otherwise specified.

Results

Compounds of Formula (I) exhibited useful pharmacological properties. As used herein, control used without the presence of an inhibitor indicates inhibition of TNF-α release in the $IC_{50}$.

Most of compounds of Formula (I) exhibited stronger inhibition than R406 control in a SYK dependent manner (e.g., IgG stimulation). The inhibition data ($IC_{50}$ value) of the representative compounds of Formula (I) of the present invention is shown in Table 3.

TABLE 3

TNF-α release inhibition by inhibiting SYK dependent pathway with the representative compounds of Formula (I).

| Compound no. | IgG stimulation ($IC_{50}$, nM) |
|---|---|
| R406 | 217 |
| 1 | 52 |
| 2 | 67 |
| 3 | 48 |
| 4 | 45 |
| 5 | 293 |
| 6 | 57 |
| 7 | 60 |
| 8 | 97 |
| 9 | 229 |
| 10 | n.d |
| 11 | 89 |
| 12 | 120 |
| 13 | 273 |
| 14 | 789 |
| 15 | 66 |
| 16 | 226 |
| 17 | n.d |
| 18 | n.d |
| 19 | 821 |
| 20 | n.d |
| 21 | n.d |
| 22 | n.d |
| 23 | 111 |
| 24 | 47 |
| 25 | 465 |
| 26 | 1065 |
| 27 | 43 |
| 28 | n.d |
| 29 | 70 |
| 30 | 17 |
| 31 | 197 |
| 32 | 53 |
| 33 | 60 |
| 34 | 55 | n.d.: not determined.
IgG stimulation represents SYK-dependent pathway.

3. Cellular Model for Systemic Lupus Erythematosus (SLE)

Systemic lupus erythematosus (SLE) is a chronic inflammatory autoimmune disease and can affect several organs and systems. It is characterized by high production of autoantibodies against nuclear compounds. TLR7/8/9 are responsible for nucleic acid recognition and they trigger proinflammatory responses through activation of NK-kappaB and Type I IFN production, making a bridge between the innate and the adaptive immune systems. TLR9 signaling pathway was adopted for cellular SLE model using human peripheral B cells to test potency of SYK inhibitor of Formula (I).

Methods

Human peripheral CD19+ B cells from an adult healthy donor were purchased from Sanguine Biosciences (Sherman Oaks, Calif.). B cells were cultured in 96-well plates with complete RPMI 1640 medium (Corning, Tewksbury, Mass.) supplemented with 10% heat-inactivated FBS (Life Technologies, Grand Island, N.Y.) and penicillin/streptomycin (Corning). B cells were stimulated with 1 μM ODN2006 (InvivoGen, San Diego, Calif.) and 20 ng/ml IFNα (PBL Assay Science, Piscataway, N.J.) for 3 days for toll-like receptor-9 (TLR-9)-mediated B cell growth. To differentiate naïve B cells into plasma cells, peripheral B cells were differentiated with 50 nM ODN2006 and 10 ng/ml IL-2 in a presence of various concentrations of SYK inhibitors for 6 days. Culture supernatants were collected and IgM and IgG production was measured using human IgM or IgG ELISA kit (BioLegend).
Results Compound No. 1 and 30 exhibited potent inhibition of IgG and IgM production via inhibition of TLR9 stimulated by ODN2006 and IFNα. The inhibition data ($IC_{50}$ value) of the Compound No. 1 and 30 is shown in Table 4.

TABLE 4

Inhibition of immunoglobulin production in human B cell.

| Compound No. | Immunoglobulin ($IC_{50}$, nM) | |
|---|---|---|
| | IgG | IgM |
| R406 | 369 | 180 |
| 1 | 296 | 232 |
| 30 | 188 | 90 |

4. Collagen-Induced Arthritis (CIA): Pre-Clinical Efficacy Models

CIA mouse model was induced in DBA/1J mice (Japan Charles River Breeding Laboratories, Kanagawa, Japan) with 5 to 6 weeks of age. Animals were maintained at a temperature of 20±5° C. and a relative humidity of 40~60%.

Bovine type II collagen (CII, 2 mg/ml dissolved in 0.05 M acetic acid, Chondrex, Redmond, Wash.) was emulsified in equal volumes of Freund's complete adjuvant (4 mg/ml of *Mycobacterium tuberculosis* strain H37Ra; Chondrex, Redmond, Wash.). On day 0, mice were immunized intradermally at the base of the tail with 100 μg bovine type II collagen emulsified in Freund's complete adjuvant. On day 21, all mice were boosted with an intraperitoneal injection of 100 μg type II collagen.

Method: Oral Administration of Compound

Compounds 1, 6 and R788 (reference, R406 prodrug) were used for this experiment. These compounds were dissolved in NMP/20% cyclodextrin/PEG400 5:45:50 solution and filtered by 0.25 μM membrane filter. All the test substances were administered once daily at 30 mg/kg/day by oral gavage for 3 weeks.

Method: Scoring of CIA Mice

The gradual onset of arthritis usually starts approximately 3 weeks after initial immunization. The progression of CIA was evaluated by the macroscopic scoring of paws at intervals of 3 days. The edema and swelling of each paw was scored visually as was described previously, using a scale of 0-4, where 0=no visible abnormalities, 1=mild redness or swelling of the wrist or up to three inflamed digits, 2=more than three inflamed digits or moderate redness and swelling of the ankle or wrist, 3=severe ankle and wrist inflammation, 4=extensive ankle and wrist inflammation including all digits. Therefore, the score of each mouse was calculated for the four limbs (maximum total score of 16 for each mouse) (Courtenay J S, Dallman M J, Dayan A D, et al., Immunisa- tion against heterologous type II collagen induces arthritis in mice, Nature, 1980, 283, 666-668)

Arthritis was considered to be present if the score was >2. The blind scoring was performed by four independent observers. In this study, data was calculated by following equation.

Anti-arthritic activity (%)={Arthritic score of test compound group/Arthritic score of vehicle treated group}×100

Results

Compounds of Formula (I) exhibited useful pharmacological properties. As used herein, control used without the presence of an inhibitor indicates CIA index.

In certain embodiments, compounds of Formula (I) exhibited stronger inhibition than R788 control. Specifically, Compound No. 1 of the present invention exhibited stronger inhibition in arthritis phenotype indicated by CIA than those exhibited by R788.

TABLE 5

CIA index by the representative compounds of Formula (I)

| Days | Vehicle | Compound No. 1 | Compound No. 6 | R788 |
|---|---|---|---|---|
| 4 | 100.0 | 3.0 ± 2.8 | 0.0 ± 0.0 | 36.7 ± 22.7 |
| 7 | 100.0 | 24.0 ± 9.2 | 10.9 ± 8.9 | 82.2 ± 45.2 |
| 10 | 100.0 | 40.1 ± 13.8 | 32.3 ± 11.5 | 80.3 ± 27.3 |
| 13 | 100.0 | 36.2 ± 12.0 | 45.3 ± 10.5 | 97.8 ± 25.0 |
| 17 | 100.0 | 33.5 ± 10.5 | 53.3 ± 7.4 | 73.3 ± 11.2 |
| 19 | 100.0 | 33.6 ± 10.4 | 63.4 ± 4.0 | 72.1 ± 11.2 |

While this invention has been particularly shown and described in example embodiments thereof, it will be understood by those skilled in the art that various changes in form and details may be made therein without departing from the scope of the invention encompassed by the appended claims.

5. Cellular Model for Diffuse Large B Cell Lymphoma

Several lines of evidence support the role of B cell receptor (BCR)-mediated survival signals in certain B cell malignancies such as non-Hodgkin lymphomas (NHL) including diffuse large B cell lymphoma (DLBCL). B cell receptor (BCR) signaling pathway components represent promising treatment targets in diffuse large B cell lymphoma (DLBCL) and additional B cell tumors. In order to address whether SYK inhibitor of Compounds of Formula (I), cellular viability of diffuse large B cell lymphoma (DLBCL) cells was measured on treatment of a series of concentration of SYK inhibitor. The experiment indicates whether SYK inhibitor inhibits proliferation of DLBCL cells.

Methods

The DLBCL cells, SUDHL4, SUDHL6 and OCI-LY1 derived from human monocytic cells were obtained from the American Type Culture Collection (ATCC, Manassas, Va., USA) or DSMZ (Braunschweig, Germany). These cell lines were maintained with suggested protocol of supplier. The SUDHL4, SUDHL6 and OCI-LY1 cells were seeded at $1 \times 10^5$ cells/100 μL/well into 96 well culture plate, and serially diluted compound was then added. After an 72 hours of incubation period at 37° C., cells were subjected to an ATPLite assay (PerkinElmer) to determine the cytotoxic effects of the compound. The $IC_{50}$ value of the test compound was calculated at Gradpad Prism 5 unless otherwise specified.

Results

Compound No 1 and 30 exhibited potent inhibition of proliferation of SUDHL4, SUDHL6 and OCI-LY1. The inhibition data (IC$_{50}$ value) of the representative compounds of Formula (I) of the present invention is shown in Table 6.

TABLE 6

| | Inhibition of proliferation of DLBCL cells | | |
|---|---|---|---|
| | Inhibition of proliferation (IC$_{50}$, nM) | | |
| Compound No. | SUDHL4 | SUDHL6 | OCI-LY1 |
| R406 | 3672 | 3232 | 3886 |
| 1 | 1067 | 2842 | 1833 |
| 30 | 952 | 929 | 2304 |

The entire contents of all patents published patent applications and other references cited herein are hereby expressly incorporated herein in their entireties by reference.

Those skilled in the art will recognize, or be able to ascertain using no more than routine experimentation, numerous equivalents to the specific procedures described herein. Such equivalents are considered to be within the scope of this invention and are covered by the following claims.

The invention claimed is:
1. A compound of Formula (I):

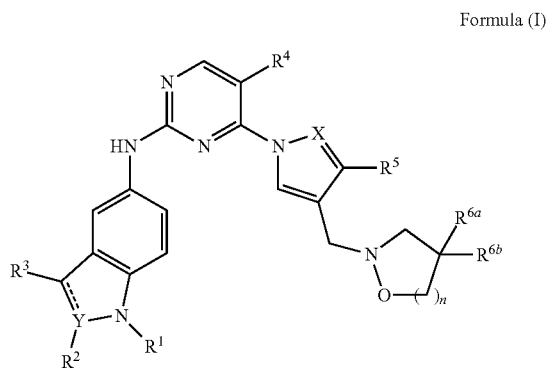

Formula (I)

Wherein:
$R^1$, $R^2$, $R^3$, $R^4$, $R^5$, $R^{6a}$, $R^{6b}$, X and Y are as described herein:
X is CH or N;
Y is C, CH or N;
n is 1 or 2;
==== is a single or a double bond, provided that if Y is C, then ==== represents a double bond;
When Y is N or CH and ==== represents a double bond, $R^2$ is absent;
$R^1$ is selected from H, $C_1$-$C_6$alkyl, $C_3$-$C_7$cycloalkyl, $C_5$-$C_8$heterocycloalkyl, aryl, arylalkyl, heteroaryl, C(O)OR$^7$, and S(O)$_2$R$^7$, wherein $C_1$-$C_6$ alkyl, $C_5$-$C_8$heterocycloalkyl, aryl, arylalkyl, or heteroaryl is optionally substituted with one or more halo, hydroxy, or OR$^7$;
When Y is C and ==== represents a double bond, or when Y is CH or N and ==== represents a single bond, then,
$R^2$ is selected from H, halo, CF$_3$, $C_1$-$C_4$alkyl and aryl, wherein the $C_1$-$C_4$alkyl or aryl is optionally substituted with one or more halo, amino, hydroxy, alkoxy, or haloalkyl;
$R^3$ is selected from H, halo, C(O)NR$^7$R$^7$, C(O)R$^7$, S(O)$_m$R$^7$, and S(O)$_m$NR$^7$R$^7$, wherein each m is 1 or 2;
$R^4$ is selected from H, halo, $C_1$-$C_6$alkyl, and $C_3$-$C_7$cycloalkyl, wherein the $C_1$-$C_6$alkyl, or $C_3$-$C_7$cycloalkyl is optionally substituted with one or more halo, amino, hydroxy, alkoxy, or haloalkyl;
$R^5$ is selected from H, halo, $C_1$-$C_6$alkyl, and $C_3$-$C_7$cycloalkyl, wherein $C_1$-$C_6$alkyl or $C_3$-$C_7$cycloalkyl is optionally and independently substituted with one or more halo, alkoxy, or haloalkyl;
$R^{6a}$ is selected from H, halo, hydroxy, CN, CH$_2$OH, NH$_2$, $C_1$-$C_6$alkyl, $C_3$-$C_7$cycloalkyl, $C_6$-$C_{10}$aryl, heteroaryl, OR$^7$, NR$^7$R$^7$, NHR$^7$, and NHC(O)R$^7$;
$R^{6b}$ is selected from H, CH$_2$OH, CH$_2$NH$_2$, and $C_1$-$C_6$alkyl;
$R^7$ is independently selected from $C_1$-$C_6$ alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, and heterocycloalkyl, wherein the $C_1$-$C_6$alkyl, $C_3$-$C_6$alkenyl, $C_3$-$C_6$alkynyl, $C_3$-$C_7$cycloalkyl, aryl, aryl($C_1$-$C_4$)alkyl, haloalkyl, heteroaryl, or heterocycloalkyl is optionally and independently substituted with one or more substituents selected from aryl, cycloalkyl, heteroaryl, heterocycloalkyl, alkyl, halo, amino, and hydroxy;
or a pharmaceutically acceptable salt thereof.

2. The compound of claim 1, wherein $R^1$ is selected from H, methyl, ethyl, propyl, isopropyl, butyl, cyclopropyl, cyclobutyl, cyclopentyl, 2-hydroxyethyl, 2-methoxyethyl, 2,2,2-trifluoroethyl, 2-fluoroethyl, ethylcarboxyl, methylsulfonyl, arylalkyl, or cyclopropylmethyl.

3. The compound of claim 1, wherein Y is C or CH.

4. The compound of claim 1, wherein $R^2$ is H, halo, CF$_3$, $C_1$-$C_4$alkyl or aryl, wherein the $C_1$-$C_4$alkyl or aryl is optionally substituted with one or more halo, alkoxy, or haloalkyl.

5. The compound of claim 1, wherein Y is N.

6. The compound of claim 1, wherein $R^3$ is H, halo, C(O)NR$^7$R$^7$, C(O)R$^7$, S(O)$_m$R$^7$, S(O)$_m$NR$^7$R$^7$, wherein each m is 1 or 2.

7. The compound of claim 6, wherein $R^3$ is selected from acetyl, propionyl, cyclopropyl carbonyl, fluoromethyl carbonyl, difluoromethyl carbonyl, trifluoromethyl carbonyl, methanesulfonyl, ethanesulfonyl, cyclopropanesulfonyl, benzenesulfonyl, p-toluenesulfonyl, N,N-dimethylaminocarbonyl, morpholinylcarbonyl, or pyrrolidinylcarbonyl.

8. The compound of claim 1, wherein $R^4$ is selected from H, F, Cl, Br, CH$_3$, CF$_3$, ethyl, cyclopropyl, or cyclobutyl.

9. The compound of claim 1, wherein $R^5$ is selected from H, Cl, Br, CH$_3$, CF$_3$, ethyl, isopropyl, cyclopropyl, cyclobutyl, or phenyl.

10. The compound of claim 1, wherein $R^{6a}$ is selected from halo, hydroxy, CN, CH$_2$OH, NH$_2$, $C_1$-$C_6$alkyl, $C_3$-$C_7$cycloalkyl, $C_6$-$C_{10}$aryl, heteroaryl, OR$^7$, NR$^7$R$^7$, NHR$^7$, and NHC(O)R$^7$.

11. A compound selected from the group consisting of
(S)-cyclopropyl(5-(4-(4-((4-hydroxyisoxazolidin-2-yl)methyl)-3-methyl-1H-pyrazol-1-yl)pyrimidin-2-ylamino)-1-methyl-1H-indol-3-yl)methanone;
(S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)-2-methylpropan-1-one;
(S)-2,2,2-trifluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;
(S)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;
(S)-ethyl 3-acetyl-5-(4-(4-((4-hydroxyisoxazolidin-2-yl)methyl)-3-methyl-1H-pyrazol-1-yl)pyrimidin-2-ylamino)-1H-indole-1-carboxylate;
(S)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone;

(S)-2,2,2-trifluoro-1-(5-(4-(4-((4-hydroxyisoxazolidin-2-yl)methyl)-3-methyl-1H-pyrazol-1-yl)pyrimidin-2-ylamino)-1H-indol-3-yl)ethanone;

(S)-cyclopropyl(5-(4-(4-((4-hydroxyisoxazolidin-2-yl)methyl)-3-methyl-1H-pyrazol-1-yl)pyrimidin-2-ylamino)-1-isopropyl-1H-indol-3-yl)methanone;

(S)-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;

(R)-2,2-difluoro-1-(5-(4-(4-((4-hydroxyisoxazolidin-2-yl)methyl)-3-methyl-1H-pyrazol-1-yl)pyrimidin-2-ylamino)-1-methyl-1H-indol-3-yl)ethanone;

(R)-cyclopropyl(1-ethyl-5-(4-(4-((4-hydroxyisoxazolidin-2-yl)methyl)-3-methyl-1H-pyrazol-1-yl)pyrimidin-2-ylamino)-1H-indol-3-yl)methanone;

(S)-cyclopropyl(5-(4-(4-((4-hydroxyisoxazolidin-2-yl)methyl)-3-methyl-1H-pyrazol-1-yl)pyrimidin-2-ylamino)-1H-indol-3-yl)methanone;

cyclopropyl(1-ethyl-5-(4-(4-((4-hydroxy-4-methylisoxazolidin-2-yl)methyl)-3-methyl-1H-pyrazol-1-yl)pyrimidin-2-ylamino)-1H-indol-3-yl)methanone;

cyclopropyl(5-(4-(4-((4-hydroxy-4-methylisoxazolidin-2-yl)methyl)-3-methyl-1H-pyrazol-1-yl)pyrimidin-2-ylamino)-1-methyl-1H-indol-3-yl)methanone;

(S)-cyclopropyl(5-(4-(4-((4-hydroxyisoxazolidin-2-yl)methyl)-3-methyl-1H-pyrazol-1-yl)pyrimidin-2-ylamino)-1-(2,2,2-trifluoroethyl)-1H-indol-3-yl)methanone;

cyclopropyl(5-(4-(4-((4-hydroxy-4-methylisoxazolidin-2-yl)methyl)-3-methyl-1H-pyrazol-1-yl)pyrimidin-2-ylamino)-1-(2,2,2-trifluoroethyl)-1H-indol-3-yl)methanone;

(S)-1-(5-(5-chloro-4-(4-((4-hydroxyisoxazolidin-2-yl)methyl)-3-methyl-1H-pyrazol-1-yl)pyrimidin-2-ylamino)-1-methyl-1H-indol-3-yl)-2,2,2-trifluoroethanone;

(S)-2,2,2-trifluoro-1-(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)ethanone;

(S)-cyclopropyl(5-(4-(4-((4-hydroxyisoxazolidin-2-yl)methyl)-3-methyl-1H-pyrazol-1-yl)-5-methylpyrimidin-2-ylamino)-1-methyl-1H-indol-3-yl)methanone;

(S)-cyclopropyl(1-ethyl-5-(5-fluoro-4-(4-((4-hydroxyisoxazolidin-2-yl)methyl)-3-methyl-1H-pyrazol-1-yl)pyrimidin-2-ylamino)-1H-indol-3-yl)methanone;

(S)-cyclopropyl(1-ethyl-5-(5-fluoro-4-(3-((4-hydroxyisoxazolidin-2-yl)methyl)-4-methyl-1H-pyrrol-1-yl)pyrimidin-2-ylamino)-1H-indol-3-yl)methanone;

(S)-cyclopropyl(1-ethyl-5-(4-(4-((4-hydroxyisoxazolidin-2-yl)methyl)-3-methyl-1H-pyrazol-1-yl)-5-methylpyrimidin-2-ylamino)-1H-indol-3-yl)methanone;

(S)-cyclopropyl(1-(2-fluoroethyl)-5-(4-(4-((4-hydroxyisoxazolidin-2-yl)methyl)-3-methyl-1H-pyrazol-1-yl)pyrimidin-2-ylamino)-1H-indol-3-yl)methanone;

cyclopropyl(1-(2-fluoroethyl)-5-(4-(4-(((S)-4-hydroxyisoxazolidin-2-yl)methyl)-3-methyl-1H-pyrazol-1-yl)pyrimidin-2-ylamino)indolin-3-yl)methanone;

(S)-cyclopropyl(5-(4-(3-cyclopropyl-4-((4-hydroxyisoxazolidin-2-yl)methyl)-1H-pyrazol-1-yl)pyrimidin-2-ylamino)-1-ethyl-1H-indol-3-yl)methanone;

(S)-2-((3-methyl-1-(2-(1-methyl-3-(methylsulfonyl)-1H-indazol-5-ylamino)pyrimidin-4-yl)-1H-pyrazol-4-yl)methyl)isoxazolidin-4-ol;

(S)-cyclopropyl(5-(4-(4-((4-hydroxyisoxazolidin-2-yl)methyl)-3-methyl-1H-pyrazol-1-yl)pyrimidin-2-ylamino)-1-(methylsulfonyl)-1H-indol-3-yl)methanone;

(S)-cyclopropyl(1-ethyl-5-(4-(3-((4-hydroxyisoxazolidin-2-yl)methyl)-4-methyl-1H-pyrrol-1-yl)pyrimidin-2-ylamino)-1H-indol-3-yl)methanone;

(S)-cyclopropyl(5-(4-(4-((4-hydroxyisoxazolidin-2-yl)methyl)-1H-pyrazol-1-yl)pyrimidin-2-ylamino)-1-methyl-1H-indol-3-yl)methanone;

(S)-2-((1-(2-(3-chloro-1,2-dimethyl-1H-indol-5-ylamino)pyrimidin-4-yl)-3-methyl-1H-pyrazol-4-yl)methyl)isoxazolidin-4-ol;

(S)-cyclopropyl(1-(2-fluoroethyl)-5-(4-(4-((4-hydroxyisoxazolidin-2-yl)methyl)-1H-pyrazol-1-yl)pyrimidin-2-ylamino)-1H-indol-3-yl)methanone;

(S)-cyclopropyl(1-(2,2-difluoroethyl)-5-(4-(4-((4-hydroxyisoxazolidin-2-yl)methyl)-1H-pyrazol-1-yl)pyrimidin-2-ylamino)-1H-indol-3-yl)methanone; and (S)-cyclopropyl(5-(4-(4-((4-hydroxyisoxazolidin-2-yl)methyl)-1H-pyrazol-1-yl)pyrimidin-2-ylamino)-1-(2,2,2-trifluoroethyl)-1H-indol-3-yl)methanone;

or a pharmaceutically acceptable salt thereof.

12. A pharmaceutical formulation comprising a compound of claim 1, in combination with a pharmaceutically acceptable carrier, diluent, or excipient.

13. A process for preparing a compound of Formula (I) according to claim 1, the process comprising:

viii. reacting a compound of formula (a) with a compound of formula (b) in a first organic solvent in the presence of a first base to give a compound of formula (c);

ix. reacting the compound of formula (c) with an aniline derivative of formula (d) in the presence of a second base, a ligand and a palladium catalyst in a second solvent to give a compound of formula (e);

x. reacting the compound of formula (e) with an amine derivative (f) in a third organic solvent in the presence of reducing agent such as $NaBH(OAc)_3$ to give a compound of Formula I;

xi. reacting the compound of formula (c) with an amine derivative (f) in a fourth organic solvent in the presence of reducing agent such as $NaBH(OAc)_3$ to give a compound of formula (g);

xii. reacting the compound of formula (g) with an aniline derivative formula (d) in the presence of a second base and a palladium catalyst to give a compound of Formula I;

or the compound of formula (e) is prepared by the following steps:

xiii. reacting a compound of formula (h) with a compound of formula (i) in the presence of a first base in a second organic solvent to give a compound of formula (j);

xiv. reacting the compound of formula (j) with a compound of formula (b) in a second organic solvent in the presence of a first base to give a compound of formula (e);

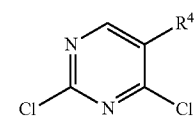

a

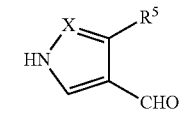

b

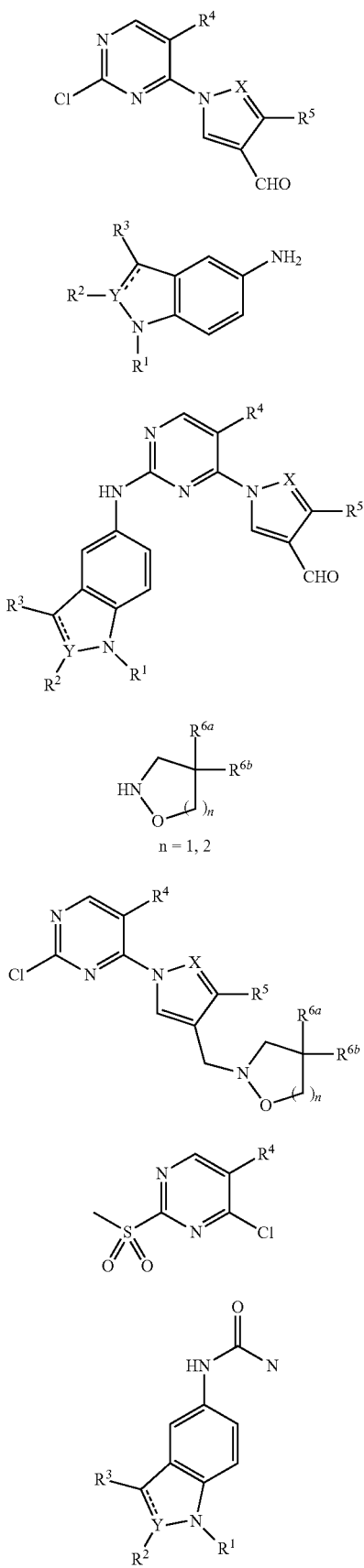

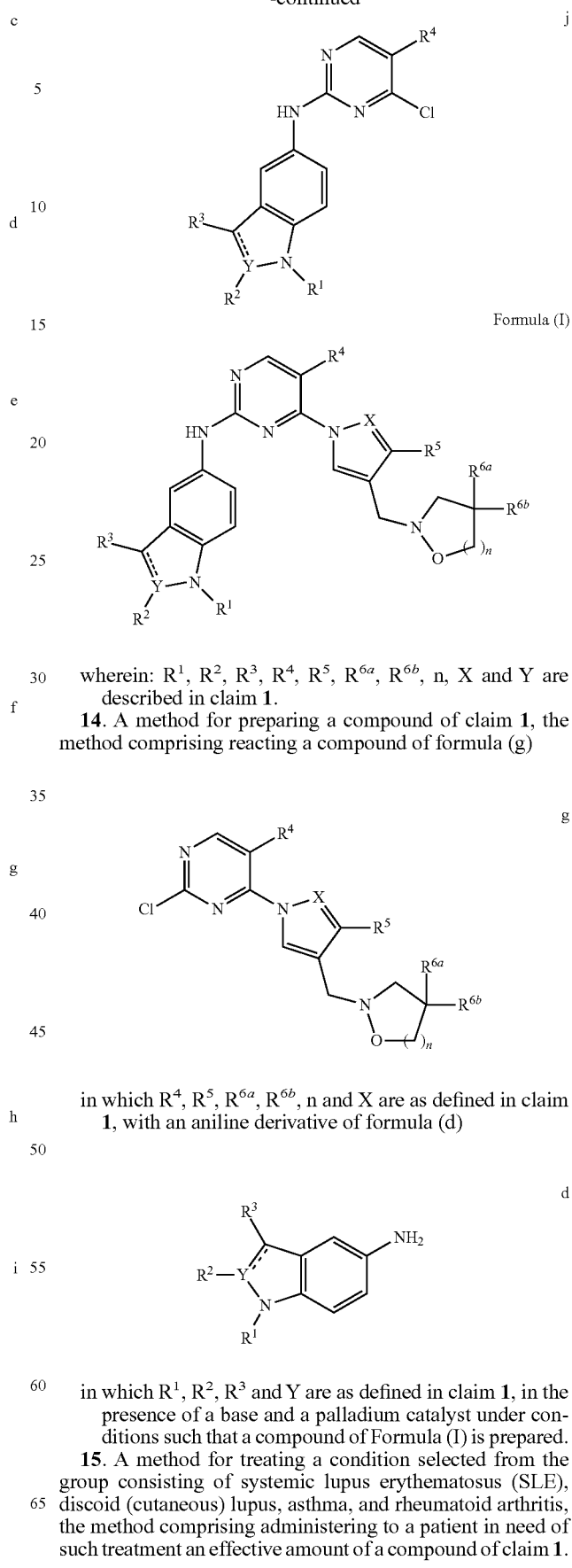

wherein: $R^1$, $R^2$, $R^3$, $R^4$, $R^5$, $R^{6a}$, $R^{6b}$, n, X and Y are described in claim 1.

14. A method for preparing a compound of claim 1, the method comprising reacting a compound of formula (g)

in which $R^4$, $R^5$, $R^{6a}$, $R^{6b}$, n and X are as defined in claim 1, with an aniline derivative of formula (d)

in which $R^1$, $R^2$, $R^3$ and Y are as defined in claim 1, in the presence of a base and a palladium catalyst under conditions such that a compound of Formula (I) is prepared.

15. A method for treating a condition selected from the group consisting of systemic lupus erythematosus (SLE), discoid (cutaneous) lupus, asthma, and rheumatoid arthritis, the method comprising administering to a patient in need of such treatment an effective amount of a compound of claim 1.

16. The method of claim 15, wherein said compound is administered singly or in combination with one or more additional therapeutic agents.

17. The method of claim 15 wherein said compound is administered via intravenous administration, subcutaneous administration, inhalation, oral administration, rectal administration, parenteral, intravitreal administration, intramuscular administration, intranasal administration, dermal administration, topical administration, optic administration, ophthalmic administration, buccal administration, tracheal administration, bronchial administration, or sublingual administration.

18. A method for treating Non-Hodgkin's Lymphomas, the method comprising administering to a patient in need thereof an effective amount of a compound of claim 1.

19. The method of claim 18, wherein the Non-Hodgkin's Lymphoma is selected from the group consisting of follicular lymphoma, mantle cell lymphoma, capsule cell lymphoma, diffuse large B cell lymphoma, T-cell lymphoma, and chronic lymphocytic lymphoma.

* * * * *